US009102774B2

(12) United States Patent
Clapper et al.

(10) Patent No.: US 9,102,774 B2
(45) Date of Patent: Aug. 11, 2015

(54) POLYMERS DERIVED FROM SECONDARY ALKYL (METH)ACRYLATES

(75) Inventors: Jason D. Clapper, Lino Lakes, MN (US); Kevin M. Lewandowski, Inver Grove Heights, MN (US); Dennis E. Vogel, Lake Elmo, MN (US); Kim M. Vogel, Lake Elmo, MN (US); Joshua L. Colby, Lino Lakes, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 207 days.

(21) Appl. No.: 13/881,526

(22) PCT Filed: Dec. 20, 2011

(86) PCT No.: PCT/US2011/066183
§ 371 (c)(1),
(2), (4) Date: Apr. 25, 2013

(87) PCT Pub. No.: WO2012/088126
PCT Pub. Date: Jun. 28, 2012

(65) Prior Publication Data
US 2013/0260149 A1 Oct. 3, 2013

Related U.S. Application Data

(60) Provisional application No. 61/425,317, filed on Dec. 21, 2010.

(51) Int. Cl.
C09J 7/02 (2006.01)
C09J 133/10 (2006.01)
C08F 220/10 (2006.01)
C07C 69/54 (2006.01)
C08F 220/18 (2006.01)
C09J 133/08 (2006.01)
C07C 67/04 (2006.01)

(52) U.S. Cl.
CPC ............... *C08F 220/10* (2013.01); *C07C 67/04* (2013.01); *C07C 69/54* (2013.01); *C08F 220/18* (2013.01); *C09J 7/0217* (2013.01); *C09J 133/08* (2013.01); *C09J 133/10* (2013.01); *Y10T 428/2891* (2015.01)

(58) Field of Classification Search
USPC ......................... 560/205; 526/328.5; 524/561; 428/355 AC
See application file for complete search history.

(56) References Cited

U.S. PATENT DOCUMENTS

| 3,087,962 A | 4/1963 | Bortnick |
| 3,691,140 A | 9/1972 | Silver |
| 4,166,152 A | 8/1979 | Baker |
| 4,330,590 A | 5/1982 | Vesley |
| 4,619,979 A | 10/1986 | Kotnour |
| 4,636,432 A | 1/1987 | Shibano |
| 4,656,218 A | 4/1987 | Kinoshita |
| 4,843,134 A | 6/1989 | Kotnour |
| 4,927,954 A | 5/1990 | Knopf |
| 5,045,569 A | 9/1991 | Delgado |
| 5,264,278 A | 11/1993 | Mazurek |
| 5,399,744 A | 3/1995 | Pfirmann |
| 5,574,163 A | 11/1996 | Luzzi |
| 5,602,221 A | 2/1997 | Bennett |
| 5,637,646 A | 6/1997 | Ellis |
| 5,648,425 A | 7/1997 | Everaerts |
| 5,708,109 A | 1/1998 | Bennett |
| 5,756,584 A | 5/1998 | Bennett |
| 5,804,610 A | 9/1998 | Hamer |
| 5,874,143 A | 2/1999 | Peloquin |
| 5,905,099 A | 5/1999 | Everaerts |
| 6,103,316 A * | 8/2000 | Tran et al. ..................... 427/505 |
| 7,385,020 B2 | 6/2008 | Anderson |
| 8,137,807 B2 | 3/2012 | Clapper |
| 2003/0233011 A1 | 12/2003 | Fagan |
| 2005/0081993 A1 | 4/2005 | Ilkka |
| 2005/0171374 A1 | 8/2005 | Manzer |
| 2006/0025741 A1* | 2/2006 | Osborn et al. ........... 604/385.18 |
| 2009/0012324 A1 | 1/2009 | Choi |

FOREIGN PATENT DOCUMENTS

| DE | 2044159 | 3/1972 |
| KR | 20060068252 | 6/2006 |
| WO | WO 2007/007084 | 1/2007 |
| WO | WO 2008/046000 | 4/2008 |

OTHER PUBLICATIONS

Ballantine, "Chemical Conversions using Sheet Silicates: Facile Ester Synthesis by Direct Addition of Acids to Alkenes", Journal of the Chemical Society, Chemical Communications, 1981, Issue 1, pp. 8-9.

Choi, "Iron-catalysed green synthesis of carboxylic esters by the intermolecular addition of carboxylic acids to alkenes", Chemical Communication, 2008; Issue 6, pp. 777-779.

Cristol, "Bridged Polycyclic Compounds. XIX. Some Addition and Solvolysis Reactions in Norbornane Systems," Journal of the American Chemical Society, Oct. 1962; vol. 84, Issue 20, pp. 3918-3925.

Feiring, "Design of very transparent fluoropolymer resists for semiconductor manufacture at 157 nm," Journal of Fluorine Chemistry, Jul. 1, 2003; vol. 122, No. 1, pp. 11-16.

Kurata, "Secondary Alcohol Ethoxylates: Physical Properties and Applications," In Monohydric Alcohols; Wickson, E.; ACS Symposium Series, American Chemical Society: Washington, D.C., 1981; pp. 113-157.

Kuusk, "Esterification of Acrylic Acid with Alkenes", *Eesti NSV Teaduste Akadeemia Toimetised*, 22, Koide, Keema. Geoloogia. 1973, NR.4. pp. 312-316. (English language translation included from the Publication of the Academy of Sciences of the Estonian Soviet Republic, vol. 22, Chemistry; Geology, 1973, No. 4, pp. 1-2.).

(Continued)

*Primary Examiner* — Vu A Nguyen
(74) *Attorney, Agent, or Firm* — Jean A. Lown

(57) ABSTRACT

Polymers, particularly those used in pressure-sensitive adhesives, are prepared from a mixture of structural isomers of a secondary alkyl (meth)acrylate monomer. The adhesives are characterized by exhibiting an overall balance of adhesive and cohesive characteristics and exceptional adhesion to low surface energy substrates.

13 Claims, No Drawings

(56) References Cited

OTHER PUBLICATIONS

Kuusk, "Esterification of Acrylic Acid with Alkenes C6-C12," *Tezisy Dokl.—Konf. Molodykh Uch. Sint. Issled. Biol. Akt.*, 1974; 39. (English language translation included from the Academy of Sciences of the Latvian Socialist Republic—Institute of Organic Synthesis; Conference of the Young Scientists for Synthesis and Research of Biologically Active Compounds; Thesis Reports; Publisher "Zinatna", Riga, 1974, pp. 1-2.).

Kuusk, "Esterification of α,β-unsaturated acids with Octene-1 Compounds," *Eesti NSV Teaduste Akadeemia Toimetised*, 1977; 26(2):150-2. (English language translation included from Publication of the Academy of Sciences of the Estonian Soviet Republic, vol. 26, Chemistry; Geology, 1977, No. 2, pp. 1-4).

Kuusk and Faingold, "Esterification of Acrylic Acid with 1-Octenes," *Eesti NSV Teaduste Akadeemia Toimetised*, 1973; 22(3):212-216. (English language translation included from the Academy of Sciences of the Estonian Soviet Republic, vol. 22, Chemistry; Geology, 1973, No. 3, pp. 1-7.).

Li, "Brønsted Acid Catalyzed Addition of Phenols, Carboxylic Acids, and Tosylamides to Simple Olefins," Organic Letters, 2006, vol. 8, No. 19, pp. 4175-4178.

Ndong Mebah, "A convenient use of polyphosphoric acid in the esterification reaction between (meth)acrylic acid and (cyclo)alkenes", New Journal of Chemistry, 1993, vol. 17, No. 12, pp. 835-841.

Patwardhan, "Esterification of carboxylic acids with olefins using cation exchange resins as catalysts", Reactive Polymers, 1990, vol. 13, pp. 161-176.

Rosenfeld, "Hydroamination and Hydroalkoxylation Catalyzed by Triflic Acid. Parallels to Reactions Initiated with Metal Triflates", Organic Letters, 2006, vol. 8, No. 19, pp. 4179-4182.

Stevens, "A New Route for Alcohols: Fully integrated continuous process results in biodegradable alcohols which can be used for detergent production" Chemical Engineering Progress, Jul. 1968, vol. 64, No. 7, pp. 61-66.

Wakabayashi "Studies on s-Triazines. I. Cotrimerization of Trichloroacetonitrile with Other Nitriles," Bulletin of the Chemical Society of Japan, 1969; vol. 42, pp. 2924-2931.

Yarbrough, "Contact Angle Analysis, Surface Dynamics, and Biofouling Characteristics of Cross-Linkable, Random Perfluoropolyether-Based Graft Terpolymers", Macromolecules, 2006, vol. 39, No. 7, pp. 2521-2528.

International Search Report for PCT/US2001/066183, 3 pages.

\* cited by examiner

POLYMERS DERIVED FROM SECONDARY ALKYL (METH)ACRYLATES

CROSS-REFERENCE TO RELATED APPLICATION

The present application claims priority to U.S. Provisional Patent Application Ser. No. 61/425,317, filed on Dec. 21, 2010, which is incorporated herein by reference.

BACKGROUND

Pressure-sensitive adhesive tapes are virtually ubiquitous in the home and workplace. In its simplest configuration, a pressure-sensitive adhesive tape comprises an adhesive and a backing, and the overall construction is tacky at the use temperature and adheres to a variety of substrates using only moderate pressure to form the bond. In this fashion, pressure-sensitive adhesive tapes constitute a complete, self-contained bonding system.

Pressure-sensitive adhesives (PSAs) are usually classified as those possessing properties such as the following: (1) aggressive and permanent tack; (2) adherence with no more than finger pressure; (3) sufficient ability to hold onto an adherend; and (4) sufficient cohesive strength to be removed cleanly from the adherend. Materials that have been found to function well as PSAs include polymers designed and formulated to exhibit the requisite viscoelastic properties resulting in a desired balance of tack, peel adhesion, and shear holding power. PSAs are characterized by being normally tacky at room temperature (e.g., 20° C.). PSAs do not embrace compositions merely because they are sticky or adhere to a surface.

These adhesive characteristics are assessed generally by means of tests which are designed to individually measure tack, adhesion (peel strength), and cohesion (shear holding power), as noted in A. V. Pocius in *Adhesion and Adhesives Technology: An Introduction*, 2$^{nd}$ Ed., Hanser Gardner Publication, Cincinnati, Ohio, 2002. These measurements taken together constitute the balance of properties often used to characterize a PSA.

With broadened use of pressure-sensitive adhesive tapes over the years, performance requirements have become more demanding. Shear holding capability, for example, which originally was intended for applications supporting modest loads at room temperature, has now increased substantially for many applications in terms of operating temperature and load. So-called high performance pressure-sensitive adhesive tapes are those capable of supporting loads at elevated temperatures for 10,000 minutes. Increased shear holding capability has generally been accomplished by crosslinking the PSA, although considerable care must be exercised so that high levels of tack and adhesion are retained in order to retain the aforementioned balance of properties.

There are a wide variety of pressure-sensitive adhesive (PSA) materials available today that include natural crude or synthetic rubbers, block copolymers, and (meth)acrylic-based polymeric compositions. (Meth)acrylic-based PSAs in particular have been the focus of a great deal of development over the last half century as the performance demands for PSAs have increased. (Meth)acrylic-based PSAs may be closely tailored to provide a number of desired attributes such as elasticity, tackiness, transparency, resistance to oxidation and sunlight, etc., as well as to have the necessary degree of adhesion and cohesion for demanding tape applications. The (meth)acrylic-based PSAs are usually (meth)acrylic ester PSAs, which are also referred to as (meth)acrylate PSAs or PSA (meth)acrylates. That is, these PSAs include a poly (meth)acrylate material.

Central to all PSAs is a desired balance of adhesion and cohesion that is often achieved by optimizing the physical properties of the acrylic elastomer, such as glass transition temperature and modulus. For example, if the glass transition temperature (Tg) or modulus of the elastomer is too high, the Dahlquist criterion for tack (storage modulus less than $3 \times 10^6$ dynes/cm$^2$ at room temperature and oscillation frequency of 1 Hz) will not be met, and the material will not be tacky and is not useful by itself as a PSA material. Often in this case, low molecular weight, high Tg resin polymers (tackifiers) or low molecular weight, low Tg polymers (plasticizers) are used to modulate the Tg and modulus into an optimal PSA range.

(Meth)acrylic ester PSAs of today are typically an elastomeric polymer prepared using a low Tg non-polar monomer. Two widely used low Tg acrylates in PSAs are 2-ethylhexyl acrylate (EHA) and isooctyl acrylate (IOA), each providing an alkyl chain of eight carbon atoms (C$_8$). Longer or shorter alkyl chains have a number of disadvantages in terms of PSA performance. For example, shorter alkyl chain (e.g., butylacrylate-C$_4$) will significantly increase both the Tg and modulus of the elastomer, possibly increasing the room temperature storage modulus above $3 \times 10^6$ dynes/cm$^2$. Alternatively, longer linear alkyl chains (e.g., octadecyl acrylate-C$_{18}$) can lead to crystalline groups within the polymer that will also significantly reduce its degree of tack.

SUMMARY

The present disclosure provides a solution to the problems associated with incorporating longer linear alkyl chains into (meth)acrylate polymers, particularly those used in pressure-sensitive adhesives (PSAs).

The compositions, particularly pressure-sensitive adhesive compositions, of this disclosure relate to the use of a mixture of structural isomers of secondary alkyl (meth)acrylate monomers, which form polymers with unique and improved properties over comparable, commonly used PSA (meth) acrylate polymers. The use of a mixture of structural isomers results in a depressed crystalline temperature (Tc) for polymers made therefrom, compared to polymers made using a single long alkyl chain (meth)acrylate. By decreasing the Tc, long chain alkyl (meth)acrylates can be formulated into PSAs with a number of beneficial characteristics, such as the ability to formulate with non-polar tackifiers. PSAs described herein exhibit excellent peel strength on both stainless steel and high density polyethylene (HDPE), which is a very low surface energy substrate to which (meth)acrylic ester PSAs typically have difficulty adhering.

In one embodiment, the present disclosure provides a (meth)acrylate polymer, particularly a pressure-sensitive adhesive composition that includes a (meth)acrylate polymer, including interpolymerized monomers that include at least three structural isomers of a secondary alkyl (meth)acrylate of Formula (I):

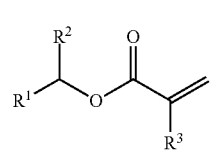

(I)

wherein:
R$^1$ and R$^2$ are each independently a C$_1$ to C$_{30}$ saturated linear alkyl group (it will be understood that in this formula R$^1$ and R$^2$ are not joined together to form a ring);
the sum of the number of carbons in R$^1$ and R$^2$ is 7 to 31; and
R$^3$ is H or CH$_3$.

In one aspect, a (meth)acrylate polymer, particularly one used in a pressure-sensitive adhesive, includes the interpolymerized reaction product of: (a) at least three structural isomers of a secondary alkyl (meth)acrylate of Formula (I); optionally (b) a (meth)acrylic acid ester of a $C_1$-$C_{32}$ alkanol; optionally (c) an acid-functional, ethylenically unsaturated monomer; optionally (d) a non-acid-functional, ethylenically unsaturated polar monomer; optionally (e) a vinyl monomer; and optionally (f) a multifunctional (meth)acrylate.

In one embodiment, the present disclosure provides a (meth)acrylate polymer, particularly a pressure-sensitive adhesive composition that includes a (meth)acrylate polymer, including at least three structural isomers of a moiety of Formula (II):

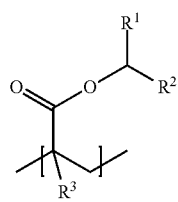
(II)

wherein $R^1$, $R^2$, and $R^3$ are as defined for Formula (I). In certain embodiments, a (meth)acrylate polymer includes at least three structural isomers of a moiety of Formula (II); and at least one moiety of a monomer selected from those listed as (b) through (f) above.

The present disclosure also provides a method of preparing an alkyl (meth)acrylate starting with an olefin, which is typically significantly less expensive than a similarly structured alkyl alcohol. This method can lead to a less expensive route to the acrylic monomer and ultimately to a PSA with equivalent performance but lower cost compared to current products.

In one embodiment, the present disclosure provides a method of making a mixture of structural isomers of a secondary alkyl (meth)acrylate of Formula (I):

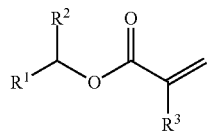
(I)

wherein:

$R^1$ and $R^2$ are each independently a $C_1$ to $C_{30}$ saturated linear alkyl group (it will be understood that in this formula $R^1$ and $R^2$ are not joined together to form a ring);

the sum of the number of carbons in $R^1$ and $R^2$ is 7 to 31; and $R^3$ is H or $CH_3$;

wherein the method comprises reacting (meth)acrylic acid with an olefin having a single unsaturation in the presence of a fluorinated sulfonic acid.

The present disclosure also provides a mixture of structural isomers of a secondary alkyl (meth)acrylate of Formula (I):

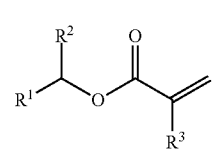
(I)

wherein:

$R^1$ and $R^2$ are each independently a $C_1$ to $C_{30}$ saturated linear alkyl group; the sum of the number of carbons in $R^1$ and $R^2$ is 7 to 31; and $R^3$ is H or $CH_3$;

wherein the 2-alkyl (meth)acrylate isomer is less than 35 mole-% of the total mixture of secondary alkyl (meth)acrylate isomers. A polymer made from this mixture is also provided.

Also provided is a method of making a mixture of structural isomers of a secondary alkyl (meth)acrylate of Formula (I):

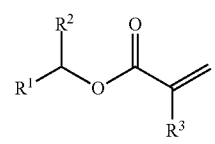
(I)

wherein:

$R^1$ and $R^2$ are each independently a $C_1$ to $C_{30}$ saturated linear alkyl group; the sum of the number of carbons in $R^1$ and $R^2$ is 7 to 31; and $R^3$ is H or $CH_3$;

wherein the method involves reacting (meth)acrylic acid with an olefin having a single unsaturation, wherein the olefin has been pre-treated with an acid to give a mixture of olefin isomers. This method preferably results in less than 35 mole-% of the 2-alkyl (meth)acrylate isomer, based on the total moles of the mixture of secondary alkyl (meth)acrylate isomers.

A (meth)acrylate polymer (that is particularly suitable for use in a pressure-sensitive adhesive polymer) is provided that includes interpolymerized monomers that include:

a) at least three structural isomers of a secondary alkyl (meth)acrylate of Formula (I):

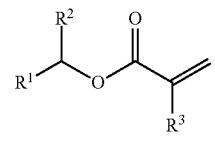
(I)

wherein:

$R^1$ and $R^2$ are each independently a $C_1$ to $C_{30}$ saturated linear alkyl group (it will be understood that in this formula $R^1$ and $R^2$ are not joined together to form a ring);

the sum of the number of carbons in $R^1$ and $R^2$ is 7 to 31; and $R^3$ is H or $CH_3$; and b) at least one monomer selected from: i) a (meth)acrylic acid ester of a $C_1$-$C_{32}$ alkanol; ii) an acid-functional, ethylenically unsaturated monomer; iii) a non-acid-functional, ethylenically unsaturated polar monomer; iv) a vinyl monomer; and v) a multifunctional (meth)acrylate. In certain embodiments, the 2-alkyl (meth)acrylate isomer of the three structural isomers used to prepare this polymer is less than 35 mole-% of the total mixture of secondary alkyl (meth)acrylate isomers.

The polymers, particularly the pressure-sensitive adhesive polymers, of the present disclosure may optionally be prepared from other monomers, crosslinkers, and additives. In particular, the pressure-sensitive adhesive may further include a tackifier.

The pressure-sensitive adhesives of this disclosure provide the desired balance of tack, peel adhesion, and shear holding power, and further conform to the Dahlquist criterion for tack (storage modulus less than $3 \times 10^6$ dynes/cm$^2$ at room temperature and oscillation frequency of 1 Hz).

Another embodiment of the present disclosure is a substrate coated with a pressure-sensitive adhesive of the present disclosure.

As used herein the term "(meth)acrylic" or "(meth)acrylate" is inclusive of both acrylic and methacrylic (or acrylate and methacrylate).

As used herein "$C_1$-$C_{32}$ alkanol (meth)acrylate" refers to a (meth)acrylate ester of a $C_1$-$C_{32}$ alkanol.

The term "aliphatic group" means a saturated or unsaturated linear or branched hydrocarbon group. This term is used to encompass alkyl, alkenyl, and alkynyl groups, for example.

The term "alkyl group" means a saturated linear or branched hydrocarbon group including, for example, methyl, ethyl, isopropyl, t-butyl, heptyl, dodecyl, octadecyl, amyl, 2-ethylhexyl, and the like. The term "alkylene group" refers to a divalent alkyl group.

The term "heteroalkyl group" means an alkyl group having at least one —$CH_2$— replaced with a heteroatom such as O or S. In many embodiments, the heteroalkyl group is a monovalent polyether group. The term "heteroalkylene group" refers to a divalent heteroalkyl group. In many embodiments, the heteroalkylene group is a divalent polyether group.

The term "alicyclic group" means a cyclic hydrocarbon group having properties resembling those of aliphatic groups. The term "aromatic group" or "aryl group" means a mono- or polynuclear aromatic hydrocarbon group.

When a group is present more than once in a formula described herein, each group is "independently" selected, whether specifically stated or not. For example, when more than one R group is present in a formula, each R group is independently selected.

The terms "comprises" and variations thereof do not have a limiting meaning where these terms appear in the description and claims.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

As used herein, "a," "an," "the," "at least one," and "one or more" are used interchangeably.

As used herein, the term "or" is generally employed in its usual sense including "and/or" unless the content clearly dictates otherwise. The term "and/or" means one or all of the listed elements or a combination of any two or more of the listed elements.

All numbers are herein assumed to be modified by the term "about" and preferably with the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used. The recitation of numerical ranges by endpoints includes all numbers subsumed within that range (e.g., 1 to 5 includes 1, 1.5, 2, 2.75, 3, 3.80, 4, and 5). All parts recited herein, including those in the Example section below, are by weight unless otherwise indicated.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

The (meth)acrylate polymers of the present disclosure are particularly useful in pressure-sensitive adhesives.

In one embodiment, the present disclosure provides a polymer, particularly a pressure-sensitive adhesive composition that includes a polymer, prepared from monomers (or including interpolymerized monomers), wherein the monomers include at least three structural isomers of a secondary alkyl (meth)acrylate of Formula (I):

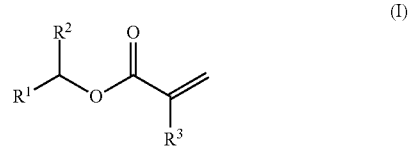

wherein:
$R^1$ and $R^2$ are each independently a $C_1$ to $C_{30}$ saturated linear alkyl group (it will be understood in this formula $R^1$ and $R^2$ are not joined together to form a ring);
the sum of the number of carbons in $R^1$ and $R^2$ is 7 to 31; and
$R^3$ is H or $CH_3$.

In one embodiment, the present disclosure provides a (meth)acrylate polymer, particularly a pressure-sensitive adhesive composition that includes a (meth)acrylate polymer, including at least three structural isomers of a moiety of Formula (II):

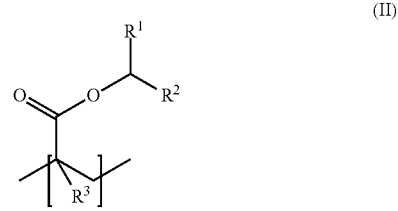

wherein $R^1$, $R^2$, and $R^3$ are as defined for Formula (I).

In certain embodiments of Formulas (I) and (II), $R^1$ and $R^2$ are each independently a $C_1$ to $C_{16}$ saturated linear alkyl and the sum of the number of carbons in $R^1$ and $R^2$ is 7 to 17.

In certain embodiments of Formulas (I) and (II), $R^1$ and $R^2$ are each independently a $C_1$ to $C_{14}$ saturated linear alkyl and the sum of the number of carbons in $R^1$ and $R^2$ is 11 to 15.

In certain embodiments of Formulas (I) and (II), $R^1$ and $R^2$ are each independently a $C_1$ to $C_6$ saturated linear alkyl and the sum of the number of carbons in $R^1$ and $R^2$ is 7 to 11.

In certain embodiments of Formulas (I) and (II), $R^1$ and $R^2$ are each independently a $C_1$ to $C_{16}$ saturated linear alkyl and the sum of the number of carbons in $R^1$ and $R^2$ is 9 to 17.

Long linear alkyl chains (e.g., 1-octadecyl acrylate-$C_{18}$) can lead to crystalline groups within the polymer that will significantly reduce its degree of tack. If the crystalline temperature can be suppressed, longer chain alkyl acrylates can have a number of beneficial PSA properties over traditional $C_8$ acrylates such as reduced Tg for broader use temperatures, lower storage modulus for quickly conforming and adhering to substrates, and lower polarity for adhering to low surface energy substrates to name a few. The branching pattern of the alkyl (meth)acrylate monomers of Formula (I) (or moieties of Formula (II)) allows the use of long alkyl chain structures while avoiding significant increases in crystalline temperature (Tc) that would decrease PSA performance. Furthermore, use of a mixture (e.g., blend) of structural isomers of the alkyl (meth)acrylate monomers of Formula (I) (or moieties of Formula (II)) has the added effect of depressing the crystalline temperature compared to traditional single structural isomer long chain linear or secondary alkyl acrylates. Depressing the Tc of long chain alkyl acrylates has many advantages in PSA materials including a broader use temperature range, improved rheological behavior, and greater compatibility with a wide range of PSA additives. Preferably, a pressure-sensitive adhesive of the present disclosure has a Tc of ≤0° C.

Monofunctional, low Tg, acrylic monomers typically used in PSAs are predominantly derived from the esterification of a primary alkyl alcohol with (meth)acrylic acid resulting in a (meth)acrylic ester monomer. Alternatively, (meth)acrylate monomers of Formula (I) can be prepared using the reaction of a (meth)acrylic acid with an olefin having a single unsaturation (e.g., an alpha-olefin), resulting in a number of branched structural isomers, as the double bond of the olefin compound is able to migrate along the chain before the addition of the (meth)acrylic acid. An example of the generation of dodecyl acrylate from both the secondary alcohol and dodecene is shown below (Scheme Ia and Scheme Ib), demonstrating the formation of a mixture of structural isomers in the latter case. This mixture of isomers in Scheme Ib results from scrambling of the double bond.

In addition to the generation of multiple structural isomers as shown in Scheme Ib, an additional advantage of this synthetic pathway is the generally lower cost of the olefin starting materials compared to similarly structured alkyl alcohols. Particularly for long chain acrylates ($C_{12}$ and greater), secondary alkyl alcohols can become very expensive while a similar alpha-olefin such as dodecene is relatively inexpensive.

Scheme Ia

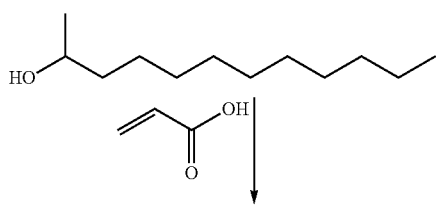

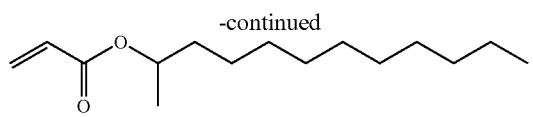

Scheme Ib

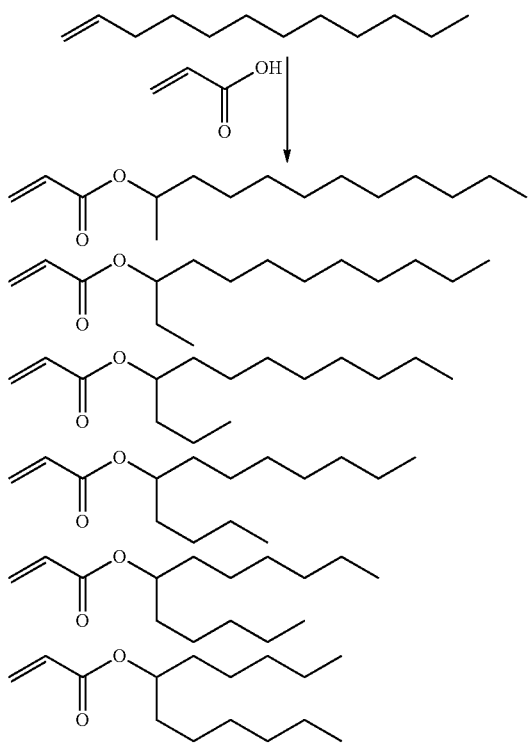

Although Scheme Ib is shown using an alpha-olefin, other olefins having a single unsaturation can be used. Examples of useful olefin starting materials include linear alpha and internal olefins such as 1-octene, 2-octene, 3-octene, 4-octene, 1-nonene, 2-nonene, 3-nonene, 4-nonene, 1-decene, 5-decene, 1-undecene, 1-dodecene, 1-tridecene, 1-tetradecene, 7-tetradecene, 1-pentadecene, 1-hexadecene, 1-heptadecene, 1-octadecene, 1-nonadecene, 1-eicosene, 9-heneicosene, 1-docosene, 9-tricosene, 1-tetracosene, 1-octacosene, 1-triacontene, as well as mixtures thereof. The olefin starting materials may be single compounds or mixtures of compounds such as those sold under the trade names NEODENE (Shell Chemicals) and ALPHAPLUS (Chevron Phillips Chemical Company), or recycled reactants from a previous reaction such as a mixture of 1-octene, 2-octene, 3-octene, and 4-octene. Any of these alkenes can be derived from bio-based sources. Additionally, the (meth)acrylic acid can be derived from bio-based sources.

Thus, the present disclosure provides a method for the production of alkyl acrylates and alkyl methacrylates based on the esterification of acrylic acid or methacrylic acid with an olefin having a single unsaturation (e.g., an alpha-olefin) in the presence of a fluorinated sulfonic acid (which is preferably used in a catalytic amount) as shown by example using 1-octene in Scheme II (in this scheme, R is H or $CH_3$ and $Rf-SO_3H$ represents a perfluorinated sulfonic acid, which is an exemplary fluorinated sulfonic acid).

Scheme II

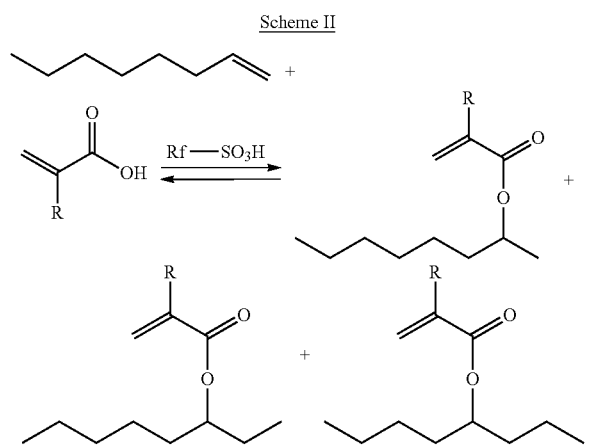

Embodiments of this method are very economical and provide high purity products. Once a typical reaction reaches equilibrium the yield can be increased by using an excess of either the acid or the olefin. The reagent used in excess, for example, can then be reclaimed and recycled. At low concentrations (e.g., no greater than about 5 mole percent), fluorinated sulfonic acids seem to be unique in the ability to allow this reaction to reach equilibrium at lower temperatures using shorter reaction times while reducing the formation of byproducts.

In an embodiment of the present disclosure for making a mixture of structural isomers of a secondary alkyl (meth)acrylate of Formula (I) as described herein, the method involves reacting (meth)acrylic acid with an olefin having a single unsaturation (e.g., an alpha-olefin) in the presence of a fluorinated sulfonic acid.

Preferred fluorinated sulfonic acids are of the formula $R^4$—$(CF_2$—$SO_3H)_n$, wherein n is one or two, and $R^4$ is a fluorine (when n is 1), a carboxylic acid group (when n is 1), a $C_1$-$C_{12}$ alkyl group (when n is 1), a $C_1$-$C_{12}$ alkylene group (when n is 2), a fluorinated (preferably, perfluorinated) $C_1$-$C_{12}$ alkyl group (when n is 1), a fluorinated (preferably, perfluorinated) $C_1$-$C_{12}$ alkylene group (when n is 2), a perfluoroether $C_1$-$C_{12}$ heteroalkyl group (when n is 1), or a perfluoroether $C_1$-$C_{12}$ heteroalkylene group (when n is 2). Preferably, the sulfonic acid is perfluorinated. Examples of $R^4$ groups include $CF_3CF_2OCF_2$—, $CF_3CF_2OCF_2CF(CF_3)OCF_2$—, HO(O)C—, $CF_3$—, $C_3F_7$—, $C_4F_{11}$—, $C_7H_{15}$—, $CF_3CHF$—, —$CF_2$—O—$CF_2$—, —$(CF_2)_3OCF_2$—, —$(CF_2)_5OCF_2$—, and —$(CF_2)_7OCF_2$—. Examples of fluorinated sulfonic acids include trifluoromethanesulfonic acid, nonafluorobutane-1-sulfonic acid, $CF_3CF_2O(CF_2)_2SO_3H$, $CF_3CF_2OCF_2CF(CF_3)OCF_2CF_2SO_2H$, HO(O)CCF_2SO_3H, $C_2F_5SO_3H$, $C_4F_9SO_3H$, $C_6F_{13}SO_3H$, $C_8H_{17}SO_3H$, $CF_3CHFCF_2SO_3H$, $O(CF_2CF_2SO_3H)_2$, $HO_3S(CF_2)_4O(CF_2)_2SO_3H$, and $HO_3S(CF_2)_6O(CF_2)_2SO_3H$, $HO_3S(CF_2)_8O(CF_2)_2SO_3H$.

Another example of a fluorinated sulfonic acid is a sulfonated tetrafluoroethylene based fluoropolymer-copolymer available under the tradename NAFION NR50 (E.I. du Pont de Nemours), which has the general Formula (III):

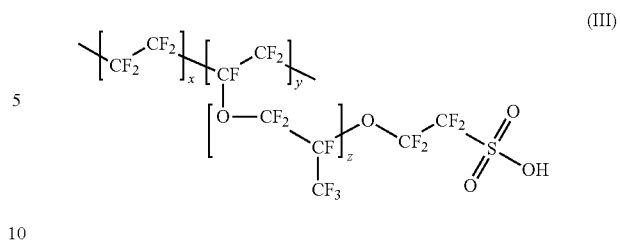

wherein x, y, and z are selected such that the sulfonic acid equivalent weight is less than or equal to 1250.

Although esterification of carboxylic acids with olefins using acid catalysis is known, with other acid catalysts typical conditions require temperatures of 100-220° C. and reaction times of 2-3 hours to reach equilibrium with generally low productions of the desired products (e.g., 45% conversion).

Preferably, the esterification of acrylic acid or methacrylic acid with an olefin according to the present disclosure can provide product yields (conversions) of at least 50%, at least 60%, or at least 70%. Significantly, because fewer undesired by-products are formed using the method of the present disclosure, unreacted starting materials can be reclaimed and recycled. Thus, even though these reactions don't go to completion because they reach an equilibrium mixture of reactants and products, if yields were calculated based on reactants consumed, reaction yields could be considered close to quantitative.

For the esterification of acrylic acid or methacrylic acid with an olefin according to the present disclosure, temperature of the reaction and concentration of the fluorinated sulfonic acid can vary, depending on the desired reaction time to reach equilibrium. For example, if the reaction is carried out at a temperature of 90° C. when the fluorinated sulfonic acid concentration is at least 2 mole percent acid, equilibrium can be reached within 4 hours. If the temperature is lowered to 70° C. at 2 mole percent fluorinated sulfonic acid, equilibrium can be reached within 18 hours. Alternatively, equilibrium can be reached within 18 hours if the temperature is raised to 120° C. and the fluorinated sulfonic acid concentration is lowered to 0.1 mole percent. Higher fluorinated sulfonic acid concentrations and/or higher temperatures can get the reaction times down to less than 1 hour if desired. In the reaction of the present disclosure, a typical concentration of a fluorinated sulfonic acid is at least 0.01 mole percent, and often up to 10 mole percent acid. A typical temperature of reaction is at least 40° C., and often up to 150° C. It will be understood that the temperature of any one reaction can vary, e.g., a reaction can be held at a first temperature for a first period of time, and raised or lowered to a second temperature for a second period of time. A typical reaction time (to equilibrium) is at least 5 minutes, and often up to 48 hours.

When the esterification reaction is carried out with an alpha-olefin (such as 1-octene), a mixture of secondary (meth)acrylate products is formed (such as a mixture of 2-octyl(meth)acrylate, 3-octyl meth)acrylate, and 4-octyl(meth)acrylate). The product mixture may contain all possible secondary (meth)acrylate isomers. The relative amounts of the (meth)acrylate isomers may vary considerably depending on the chain length of the olefin starting material and the reaction conditions used (such as temperature and catalyst concentration).

The alpha-olefin starting material may also be isomerized to a mixture of olefins prior to addition of (meth)acrylic acid by reaction with the acid catalyst. Typically, the catalyst used for this pre-isomerization process is the same as that used for the reaction between the olefin and (meth)acrylic acid. The temperature of the pre-isomerization process is typically 70-100° C. Often, an equal distribution of the internal isomers is obtained with only a small amount of the alpha-olefin. With this pre-isomerization process, the resultant secondary (meth)acrylate products are more equally distributed resulting in less of the 2-alkyl (meth)acrylate isomer and more internal (meth)acrylate isomers (such as 3-, 4-, and 5-alkyl (meth)acrylates). Typically, the 2-alkyl (meth)acrylate isomer is less than 35 mole-% of the total mixture of alkyl (meth)acrylate isomers. Generally, as the percentage of the 2-isomer decreases in the various secondary (meth)acrylate blends, the Tc and Tm of the resulting polymer decreases accordingly.

Thus, the present disclosure provides a mixture of structural isomers of a secondary alkyl (meth)acrylate of Formula (I) as described herein, wherein the 2-alkyl (meth)acrylate isomer is less than 35 mole-% of the total mixture of alkyl (meth)acrylate isomers. Such a mixture can provide a novel polymer. For example, isomers of Formula (I) can be interpolymerized with at least one monomer selected from: i) a (meth)acrylic acid ester of a $C_1$-$C_{32}$ alkanol; ii) an acid-functional, ethylenically unsaturated monomer; iii) a non-acid-functional, ethylenically unsaturated polar monomer; iv) a vinyl monomer; and v) a multifunctional (meth)acrylate. Preferably, the less than 35 mole-% 2-alkyl (meth)acrylate isomer results from using the pre-isomerization reaction process.

Whether the olefin is pre-isomerized or not, the amount of 2-alkyl (meth)acrylate in the reaction product is typically 15-85 mole-% of the total (meth)acrylate product mixture. The amount of 3-alkyl (meth)acrylate in the reaction product is typically 5-50 mole-% of the total (meth)acrylate product mixture. The amount of 4-alkyl (meth)acrylate in the reaction product is typically 0.5-50 mole-% of the total (meth)acrylate product mixture. The amount of 5-alkyl (meth)acrylate and all other higher alkyl (meth)acrylates (6-through 15-alkyl (meth)acrylate) in the reaction product is typically 0-50 mole-% of the total (meth)acrylate product mixture.

In the esterification of (meth)acrylic acid with an olefin, the amount of olefin and (meth)acrylic acid can vary as desired. As mentioned above, one reagent can be used in excess relative to the other to decrease the time of the reaction and increase the yield. If one of the reagents is less expensive than the other, the less expensive one would be the one typically chosen to be in excess.

The esterification of acrylic acid or methacrylic acid with an olefin according to the present disclosure is typically carried out neat, i.e., in the absence of solvent. If desired, however, solvents such as hexane, heptane, toluene, and xylenes can be used.

An alternative method of making the (meth)acrylate monomers of Formula (I) can be carried out by esterification of a mixture of secondary alcohols. The mixture of secondary alcohols can be prepared by blending individual secondary alcohols that have been prepared separately. Another potential preparation of a structural isomer mixture of secondary alcohols involves an oxidation process that converts parrafins to secondary alcohols (see, e.g., Stevens et al., *Chem. Eng. Prog.*, Vol. 64, No. 7, pages 61-68 (1968); Kurata et al., Chapter 9, "Secondary Alcohol Ethoxylates," In *Monohydric Alcohols, ACS Symposium Series*, American Chemical Society, pages 113-157 (1981)). The alcohol products of this process maintain the same carbon distribution of the starting paraffin. Thus, secondary alcohols are produced with a random distribution along the chain, with little to no primary alcohols being formed. Alternatively, the polymer of Formula (II) may be prepared by reaction of a poly(meth)acrylic acid (or poly(meth)acrylic acid-co-alkyl acrylate) with olefins using the methods described herein or with a mixture of secondary alcohols.

In certain embodiments, the present disclosure provides a continuous process for the esterification of acrylic acid or methacrylic acid with an olefin (which may or may not have been pre-isomerized by contact with an acid catalyst). Herein, a "continuous" process is defined to be a process with continuous flow or semi-continuous flow (e.g., pulsed flow) of material(s) in and out of the reactor once the system is operating at steady state. Preferably, a "continuous" process uses a fixed-bed heterogeneous catalyst flow-through system. In a continuous process of this disclosure, a reactor, typically a tubular reactor, having an inlet for reactants and an outlet for products is charged with a fixed bed of solid acid catalyst and used to perform the desired chemical transformation(s). This reactor configuration, often described as a "packed-bed reactor," can be advantageous when compared to homogeneously catalyzed batch reactions for a number of reasons including: ease of reaction; tighter control over process variables (e.g., temperature, pressure and residence time); higher catalyst to reagent ratio (facilitating higher rates of reaction); and elimination of a catalyst filtration and/or neutralization step. As an alternative to using a packed-bed reactor configuration, other well known continuous reactor configurations may be employed such as "continuous stirred tank" reactors or "reactive distillation" reactors.

A wide variety of commercially available solid (typically, resin) acid catalysts may be used with a packed-bed reactor, for example, in a continuous process. In particular, solid acid (heterogeneous) catalysts may be advantageously used in performing the desired chemical transformation(s) disclosed herein including, but not limited to, high fluorine content aliphatic sulfonic acids (e.g., those available under the trade name NAFION) and sulfonated styrene divinylbenzene copolymers (e.g., those available under the trade name AMBERLYST). Selection of a suitable solid acid catalyst material is typically determined by cost, rate of reaction, and selectivity to desired products. One particular type of resin, macroreticular resin, is particularly preferred because it is inexpensive and available in a wide variety of different physical and/or chemical structures. Varying catalyst features such as catalyst surface area, porosity, and acidity can be tuned by varying resin properties such as the extent of crosslinking and degree of sulfonization, facilitating the selection of a suitable catalyst for each desired reaction. Selection of such features is within the skill of one skilled in the art.

In one exemplary continuous process, olefin and acid reactants (as described herein) are mixed prior to entering or upon entering the reaction zone, defined to be the volume in the tubular reactor occupied by the heterogeneous catalyst material. Time required to perform the desired reaction can vary, primarily due to catalyst type and temperature. Reactant residence time, defined as the catalyst void volume divided by the volumetric feed rate of the reactants, may be controlled, for example, by adjusting the total reactant feed rate to the reactor. Reactant residence time is typically held constant at values of at least 1 minute, and often at least 5 minutes. Reactant residence time is typically held constant at values of no greater than 120 minutes, and often no greater than 20 minutes. Reaction temperatures may be controlled with resistively heated insulating tape or by circulating heating oil from a temperature controlled bath, or other conventional methods. Typical reaction temperatures are at least 40° C., and often at least 50° C. Typical reaction temperatures are no greater than 150° C., and often at least 90° C. These temperatures produce single pass yields and selectivities in reasonable amounts of time. Reaction pressures may be controlled by a back pressure regulator placed at the outlet of the reactor unit, or other conventional methods. Typically, reaction pressures are no greater than 5 MPa, and often no greater than 1 MPa. These pressures will typically keep reagents in the liquid phase while reducing the need for specialized equipment that can withstand elevated pressures.

Whether in a continuous or batch process, after the reaction of the olefin and (meth)acrylic acid, the crude secondary (meth)acrylate product is typically purified. When an excess of olefin relative to (meth)acrylic acid is used in the reaction, the product is typically isolated by distillation to separate unreacted olefin and the secondary (meth)acrylate product. Alternatively, the crude reaction mixture can be first extracted with a basic aqueous solution (e.g., aqueous sodium bicarbonate) to remove any residual (meth)acrylic acid followed by distillation to isolate the secondary (meth)acrylate product.

During the reaction and subsequent purification procedures, a polymerization inhibitor is typically added. Suitable examples include, but are not limited to: hydroquinone (HQ); 4-methoxyphenol (MEHQ); 4-ethoxyphenol; 4-propoxyphenol; 4-butoxyphenol; 4-heptoxyphenol; hydroquinone monobenzylether; 1,2-dihydroxybenzene; 2-methoxyphenol; 2,5-dichlorohydroquinone; 2,5-di-tert-butylhydroquinone; 4-aminophenol; 2-aminophenol; 2-N,N-dimethylaminophenol; catechol monobutylether; 2,3-dihydroxyacetophenone; pyrogallol-1,2-dimethylether; t-butyl catechol; di-tertbutylnitroxide; di-tert-amylnitroxide; 2,2,6,6-tetramethylpiperidinyloxy; 4-hydroxy-2,2,6,6-tetramethyl-piperidinyloxy; 4-oxo-2,2,6,6-tetramethyl-piperidinyloxy; copper dimethyldithiocarbamate; copper salicylate; methylene blue; iron; phenothiazine; 3-oxophenothiazine; and 1,4-benzenediamine. The inhibitor or combination of inhibitors is typically added from 0.01 wt-% to 5.0 wt-%, based on the total volume of the reaction mixture.

The polymer (preferably pressure-sensitive adhesive polymer) of the present disclosure may include other monomers to modify the physical properties of the polymer produced by polymerization of at least three structural isomers of an alkyl (meth)acrylate monomer of Formula (I). Additionally, the polymers, particularly the pressure-sensitive adhesive polymers, of the present disclosure may include crosslinkers, and other additives, such as tackifiers or plasticizers. In one aspect, the polymer (preferably pressure-sensitive adhesive polymer) includes the interpolymerized reaction product of: (a) at least three structural isomers of a secondary alkyl (meth)acrylate of Formula (I); optionally (b) a (meth)acrylic acid ester of a $C_1$-$C_{32}$ alkanol; optionally (c) an acid-functional, ethylenically unsaturated monomer; optionally (d) a non-acid-functional, ethylenically unsaturated polar monomer; optionally (e) a vinyl monomer; and optionally (f) a multifunctional (meth)acrylate. In certain embodiments, the interpolymerized monomers include at least one monomer selected from a (meth)acrylic acid ester of a $C_1$-$C_{32}$ alkanol, an acid-functional, ethylenically unsaturated monomer, a non-acid-functional, ethylenically unsaturated polar monomer, and a mixture thereof, and optionally one or more of the vinyl monomer and multifunctional (meth)acrylate. In certain other embodiments, the interpolymerized monomers include an acid-functional, ethylenically unsaturated monomer.

The compositions used to form the polymers, particularly the pressure-sensitive adhesive polymers, of the present disclosure may include only a polymerized alkyl (meth)acrylate monomer of Formula (I) comprising at least three structural isomers, which may sometimes be referred to as a homopolymer. In many preferred embodiments, the composition includes 20 to 99.5, and in more preferred embodiments 50 to 95, parts by weight of a mixture of isomers of a secondary alkyl (meth)acrylate of Formula (I), relative to 100 parts total monomer.

The polymers, particularly the pressure-sensitive adhesive polymers, of the present disclosure may further comprise interpolymerized monomer units of a $C_1$-$C_{32}$ (meth)acrylate ester monomer (i.e., (meth)acrylic acid ester of a $C_1$-$C_{32}$ alkanol). These are typically distinct monomers from the compounds of Formula (I). In some embodiments, these are $C_1$-$C_{24}$, $C_1$-$C_{18}$, or $C_1$-$C_{12}$ (meth)acrylate ester monomers. Examples of monomers suitable for use as the $C_1$-$C_{32}$ (meth)acrylate ester monomer include an ester of either acrylic acid or methacrylic acid with a non-tertiary alkanol such as ethanol, 1-propanol, 2-propanol, 1-butanol, 2-butanol, 1-pentanol, 2-pentanol, 3-pentanol, 2-methyl-1-butanol, 3-methyl-1-butanol, 1-hexanol, 2-hexanol, 2-methyl-1-pentanol, 3-methyl-1-pentanol, 2-ethyl-1-butanol, 3,5,5-trimethyl-1-hexanol, 3-heptanol, 1-octanol, 2-octanol, isooctylalcohol, 2-ethyl-1-hexanol, 1-decanol, 2-propylheptanol, 1-dodecanol, 1-tridecanol, 1-tetradecanol, citronellol, dihydrocitronellol, and the like. In some embodiments, the preferred (meth)acrylate ester monomer is the ester of (meth)acrylic acid with butyl alcohol or isooctyl alcohol, or a combination thereof, although combinations of two or more different (meth)acrylate ester monomers are suitable.

In some embodiments it is desirable for the $C_1$-$C_{32}$ (meth)acrylate ester monomer to include a high Tg monomer, having a homopolymer Tg of at least 25° C., and preferably at least 50° C. Examples of suitable high Tg monomers useful in the present disclosure include, but are not limited to, t-butyl acrylate, methyl methacrylate, ethyl methacrylate, isopropyl methacrylate, n-butyl methacrylate, isobutyl methacrylate, s-butyl methacrylate, t-butyl methacrylate, stearyl methacrylate, phenyl methacrylate, cyclohexyl methacrylate, isobornyl acrylate, isobornyl methacrylate, benzyl methacrylate, 3,3,5-trimethylcyclohexyl acrylate, cyclohexyl acrylate, propyl methacrylate, and combinations thereof.

If present, a $C_1$-$C_{32}$ (meth)acrylate ester monomer is present in an amount of up 80 parts by weight, and preferably up to 45 parts by weight, based on 100 parts total monomers. If present, a $C_1$-$C_{32}$ (meth)acrylate ester monomer is present in an amount of at least 1 part by weight, and preferably at least 5 parts by weight, based on 100 parts total monomers. In certain embodiments, a $C_1$-$C_{32}$ (meth)acrylate ester monomer is present in an amount of 1 part to 45 parts, and in other embodiments 5 parts to 45 parts, by weight, based on 100 parts total monomers. When a high Tg monomer is included, the copolymer may include up to 50 parts by weight, preferably, 10 to 20 parts by weight, relative to 100 parts by weight of $C_1$-$C_{32}$ (meth)acrylate ester monomer component.

The composition used to form the polymers, particularly the pressure-sensitive adhesive polymers, of the present disclosure may further include an acid-functional monomer, wherein the acid-functional group may be an acid per se, such as a carboxylic acid, or a portion may be salt thereof, such as an alkali metal carboxylate. Useful acid-functional monomers include, but are not limited to, those selected from an ethylenically unsaturated carboxylic acid, ethylenically unsaturated sulfonic acid, ethylenically unsaturated phosphonic acid, and mixtures thereof. Examples of such compounds include those selected from acrylic acid, methacrylic acid, itaconic acid, fumaric acid, crotonic acid, citraconic acid, maleic acid, oleic acid, β-carboxyethyl(meth)acrylate, 2-sulfoethyl methacrylate, styrene sulfonic acid, 2-acrylamido-2-methylpropanesulfonic acid, vinylphosphonic acid, and mixtures thereof.

Due to their availability, an acid-functional monomer is generally selected from ethylenically unsaturated carboxylic acids (i.e., (meth)acrylic acids). When even stronger acids are desired, acidic monomers can include the ethylenically unsaturated sulfonic acids and ethylenically unsaturated phosphonic acids.

If present, an acid-functional, ethylenically unsaturated monomer is present in an amount of up 20 parts by weight, preferably up to 15 parts by weight, and more preferably up to 10 parts by weight, based on 100 parts total monomers. If present, an acid-functional, ethylenically unsaturated monomer is present in an amount of at least 0.5 parts by weight, preferably at least 1.0 part by weight, and more preferably at least 1.5 parts by weight, based on 100 parts total monomers. In certain embodiments, an acid-functional, ethylenically unsaturated monomer is present in an amount of 0.5 parts to 20 parts by weight, and in other embodiments 1.0 part to 15 parts by weight, and in still other embodiments, 1.5 parts to 10 parts by weight, based on 100 parts total monomers.

The composition used to form the polymers, particularly the pressure-sensitive adhesive polymers, of the present disclosure may further include a polar monomer. A polar monomer useful in preparing the polymer of the present disclosure is both somewhat oil soluble and water soluble, resulting in a distribution of the polar monomer between the aqueous and oil phases in an emulsion polymerization. As used herein, the term "polar monomer" is exclusive of acid-functionality and is referred to as a "non-acid-functional, ethylenically unsaturated polar monomer."

Representative examples of suitable such polar monomers include, but are not limited to, 2-hydroxyethyl(meth)acrylate; 4-hydroxybutyl(meth)acrylate; N-vinylpyrrolidone; N-vinylcaprolactam; acrylamide; mono- or di-N-alkyl substituted acrylamide; t-butyl acrylamide; dimethylaminoethyl acrylamide; N-octyl acrylamide; a poly(alkoxyalkyl) (meth)acrylate including 2-(2-ethoxyethoxy)ethyl(meth)acrylate, 2-ethoxyethyl(meth)acrylate, 2-methoxyethoxyethyl(meth) acrylate, 2-methoxyethyl methacrylate, and a polyethylene glycol mono(meth)acrylate; an alkyl vinyl ether, including vinyl methyl ether; and mixtures thereof. Preferred polar monomers include those selected from the group consisting of 2-hydroxyethyl(meth)acrylate, N-vinylpyrrolidinone, and mixtures thereof.

If present, a non-acid-functional, ethylenically unsaturated polar monomer is present in an amount of up 10 parts by weight, based on 100 parts total monomers. If present, a non-acid-functional, ethylenically unsaturated polar monomer is present in an amount of at least 0.5 parts by weight, based on 100 parts total monomers.

The composition used to form the polymers, particularly the pressure-sensitive adhesive polymers, of the present disclosure may further include one or more other vinyl monomers. When used, vinyl monomers useful in the (meth)acrylate polymer include a vinyl ester (e.g., vinyl acetate and vinyl propionate), styrene, substituted styrene (e.g., α-methyl styrene), vinyl halide, and mixtures thereof. As used herein vinyl monomers are exclusive of acid-functional monomers, acrylate ester monomers, and polar monomers.

If present, a vinyl monomer is present in an amount of up 5 parts by weight, based on 100 parts total monomers. If present, a vinyl monomer is present in an amount of at least 1.0 part by weight, based on 100 parts total monomers.

There are several crosslinking mechanisms for acrylic polymers (particularly, adhesives) including free-radical copolymerization of multifunctional, ethylenically unsaturated groups with the other monomers, and covalent or ionic crosslinking through the functional monomers, such as acrylic acid. Another method is the use of UV crosslinkers, such as copolymerizable benzophenones or post-added photocrosslinkers, such as multifunctional benzophenones and triazines. In the past, a variety of different materials have been used as crosslinking agents, e.g., polyfunctional acrylates, acetophenones, benzophenones, and triazines. Crosslinking may also be achieved using high energy electromagnetic radiation such as gamma or e-beam radiation. In this case, no additional crosslinker may be required. One or more of these mechanisms can be used with the polymers described herein.

In order to increase cohesive strength of the coated (particularly, adhesive) composition, a multifunctional (meth)acrylate may be incorporated into the blend of polymerizable monomers. A multifunctional (meth)acrylate is particularly useful for emulsion or syrup polymerization. Examples of a useful multifunctional (meth)acrylate include, but are not limited to, a di(meth)acrylate, tri(meth)acrylate, and tetra (meth)acrylate, such as 1,6-hexanediol di(meth)acrylate, a poly(ethylene glycol) di(meth)acrylate, polybutadiene di(meth)acrylate, a polyurethane di(meth)acrylate, propoxylated glycerin tri(meth)acrylate, and mixtures thereof.

If present, a multifunctional (meth)acrylate monomer is present in an amount of up 5 parts by weight, and preferably up to 1.0 parts by weight, based on 100 parts total monomers. If present, a multifunctional (meth)acrylate monomer is present in an amount of at least 0.01 parts by weight, and preferably at least 0.05 parts by weight, based on 100 parts total monomers. In certain embodiments, a multifunctional (meth)acrylate monomer is present in an amount of 0.01 parts to 5 parts by weight, and in other embodiments 0.05 parts to 1.0 parts by weight, based on 100 parts total monomers.

In some embodiments, the interpolymerized monomers can include:

a) up to 100, preferably 20 to 99.5, more preferably 50 to 95, parts by weight of a component comprising at least three structural isomers of a secondary alkyl (meth)acrylate of Formula (I);

b) 0 to 80, preferably 1 to 45, more preferably 5 to 45, parts by weight of a (meth)acrylic acid ester of a $C_1$-$C_{32}$ alkanol;

c) 0.5 to 20, preferably 1.0 to 15, more preferably 1.5 to 10, parts by weight of an acid-functional, ethylenically unsaturated monomer;

d) 0 to 10, preferably 0.5 to 10, parts by weight of a non-acid-functional, ethylenically unsaturated polar monomer;

e) 0 to 5, preferably 1 to 5 parts by weight of a vinyl monomer; and f) 0 to 5, preferably 0.01 to 5, more preferably 0.05 to 1.0, parts by weight of a multifunctional (meth)acrylate;

based on 100 parts by weight total monomers.

The polymers, particularly pressure-sensitive adhesive polymers, disclosed herein may be prepared by a variety of conventional free radical polymerization methods, including solution, radiation, bulk, dispersion, emulsion, and suspension processes. The monomer mixture may comprise a polymerization initiator, especially a thermal initiator or a photoinitiator of a type and in an amount effective to polymerize the monomers, as described below. For optical applications, solution, UV, and bulk processes are preferred. Other processes may introduce birefringence or foreign materials that may affect optic properties. The resulting adhesive copolymers of the present disclosure may be random or block copolymers.

The polymers may be prepared via suspension polymerizations as disclosed in U.S. Pat. No. 3,691,140 (Silver); U.S.

Pat. No. 4,166,152 (Baker et al.); U.S. Pat. No. 4,636,432 (Shibano et al); U.S. Pat. No. 4,656,218 (Kinoshita); and U.S. Pat. No. 5,045,569 (Delgado).

Water-soluble and oil-soluble initiators useful in preparing the (meth)acrylate polymers of the present disclosure are initiators that, on exposure to heat, generate free-radicals which initiate (co)polymerization of the monomer mixture. Water-soluble initiators are preferred for preparing the (meth)acrylate polymers by emulsion polymerization. Suitable water-soluble initiators include, but are not limited to, those selected from the group consisting of potassium persulfate, ammonium persulfate, sodium persulfate, and mixtures thereof; an oxidation-reduction initiator such as the reaction product of an above-mentioned persulfate and a reducing agent such as those selected from the group consisting of sodium metabisulfite and sodium bisulfite; and 4,4'-azobis(4-cyanopentanoic acid) and its soluble salts (e.g., sodium, potassium). The preferred water-soluble initiator is potassium persulfate. Suitable oil-soluble initiators include, but are not limited to, those selected from the group consisting of an azo compound such as VAZO 64 (2,2'-azobis(isobutyronitrile)) and VAZO 52 (2,2'-azobis(2,4-dimethylpentanenitrile)) (both available from E.I. du Pont de Nemours Co.), peroxides such as benzoyl peroxide and lauroyl peroxide, and mixtures thereof. The preferred oil-soluble thermal initiator is (2,2'-azobis(isobutyronitrile)). When used, initiators may be included in an amount up to 1 parts by weight, preferably from 0.05 to 1 parts by weight, more preferably 0.1 to 0.5 parts by weight, relative to 100 parts by weight of total monomer.

The polymerizable mixture may optionally further comprise chain transfer agents to control the molecular weight of the resultant polymer. Examples of useful chain transfer agents include, but are not limited to, those selected from the group consisting of carbon tetrabromide, alcohols, mercaptans, and mixtures thereof. When present, the preferred chain transfer agents are isooctylthioglycolate and carbon tetrabromide. If used, the polymerizable mixture may include up to 0.5 parts by weight of a chain transfer agent, typically 0.01 parts by weight to 0.5 parts by weight, and preferably 0.05 parts by weight to 0.2 parts by weight, relative to 100 parts by weight of the total monomer.

A typical solution polymerization method is carried out by adding the monomers, a suitable solvent, and an optional chain transfer agent to a reaction vessel, adding a free radical initiator, purging with nitrogen, and maintaining the reaction vessel at an elevated temperature, typically in the range of 40 to 100° C. until the reaction is completed, typically in 1 to 20 hours, depending upon the batch size and temperature. Examples of the solvent are methanol, tetrahydrofuran, ethanol, isopropanol, acetone, methyl ethyl ketone, methyl acetate, ethyl acetate, toluene, xylene, and ethylene glycol alkyl ether. Those solvents can be used alone or as mixtures thereof.

In a typical photopolymerization method, a monomer mixture may be irradiated with ultraviolet (UV) rays in the presence of a photopolymerization initiator (i.e., photoinitiators). Preferred photoinitiators are those available under the trade designations IRGACURE and DAROCUR from Ciba Specialty Chemical Corp., Tarrytown, N.Y. and include 1-hydroxy cyclohexyl phenyl ketone (IRGACURE 184), 2,2-dimethoxy-1,2-diphenylethan-1-one (IRGACURE 651), bis (2,4,6-trimethylbenzoyl)phenylphosphineoxide (IRGACURE 819), 1-[4-(2-hydroxyethoxy)phenyl]-2-hydroxy-2-methyl-1-propane-1-one (IRGACURE 2959), 2-benzyl-2-dimethylamino-1-(4-morpholinophenyl)butanone (IRGACURE 369), 2-methyl-1-[4-(methylthio)phenyl]-2-morpholinopropan-1-one (IRGACURE 907), and 2-hydroxy-2-methyl-1-phenyl propan-1-one (DAROCUR 1173). Particularly preferred photoinitiators are IRGACURE 819, 651, 184 and 2959.

Solventless polymerization methods may also be utilized to prepare the polymers, such as the continuous free radical polymerization method described in U.S. Pat. No. 4,619,979 (Kotnour et al.) and U.S. Pat. No. 4,843,134 (Kotnour et al.), the essentially adiabatic polymerization methods using a batch reactor described in U.S. Pat. No. 5,637,646 (Ellis), and the methods described for polymerizing packaged pre-adhesive compositions described in U.S. Pat. No. 5,804,610 (Hamer et al.).

The compositions of the present disclosure, particularly the pressure-sensitive adhesives, may also contain one or more conventional additives. Preferred additives include tackifiers, plasticizers, dyes, antioxidants, and UV stabilizers. Such additives can be used if they do not affect the superior properties of the pressure-sensitive adhesives, for example.

Conventional (meth)acrylic-based adhesives do not adhere well to certain substrates, such as certain types of automotive paints and low energy olefinic surfaces. Efforts have been made to improve the adhesion of (meth)acrylic-based adhesives, i.e., develop more aggressive tack, to these types of surfaces; tackifying the base acrylic polymer is commonly practiced. The tackifier is generally selected to be miscible with the (meth)acrylate polymer used to form the PSA. Suitable tackifying resins include rosins and their derivatives (e.g., rosin esters); polyterpenes and aromatic-modified polyterpene resins; coumarone-indene resins; and hydrocarbon resins such as alpha pinene-based resins, beta pinene-based resins, limonene-based resins, aliphatic hydrocarbon-based resins, aromatic-modified hydrocarbon-based resins, aromatic hydrocarbon resins, and dicyclopentadiene-based resins. In certain embodiments, the tackifier is a terpene resin, a hydrocarbon resin, a rosin resin, a petroleum resin, or combination thereof. Combinations of various tackifiers can be used if desired. These tackifying resins, if desired, can be hydrogenated to lower their color contribution to the pressure-sensitive adhesive layer.

Various types of tackifiers include phenol modified terpenes and rosin esters such as glycerol esters of rosin and pentaerythritol esters of rosin that are available under the trade names NUROZ, NUTAC (Newport Industries), PERMALYN, STAYBELITE, FORAL (Eastman). Also available are hydrocarbon resin tackifiers that typically come from C5 and C9 monomers by products of naphtha cracking and are available under the trade names PICCOTAC, EASTOTAC, REGALREZ, REGALITE (Eastman), ARKON (Arakawa), NORSOLENE, WINGTACK (Cray Valley), NEVTAC LX (Neville Chemical Co.), HIKOTACK, HIKOREZ (Kolon Chemical), NOVARES (Ruetgers N.V.), QUINTONE (Zeon), ESCOREZ (Exxon Mobile Chemical), NURES, and H-REZ (Newport Industries).

Due to the high solubility parameter of most conventional (meth)acrylic-based polymers used in pressure-sensitive adhesives and the presence of specific potential interactions between these polymeric materials and many tackifiers, a limited selection of tackifiers is available to the formulator. As a class, hydrocarbon-based tackifiers, and especially hydrogenated hydrocarbon resins, are typically unsuitable for use in polar (meth)acrylic-based adhesives formulations due to their nonpolar character.

Rosin acid based tackifiers and selected phenol-modified terpene and alpha-pinene based resins perform well in a variety of conventional (meth)acrylic-based pressure-sensitive adhesives. However, some problems are still associated with the use of this limited range of tackifiers in such (meth) acrylic-based adhesives. Tackified (meth)acrylic-based pressure-sensitive adhesive formulations are often discolored or yellow. The yellow appearance of these tackified (meth) acrylic-based pressure-sensitive adhesives is a direct result of the distinct yellow tinge inherent in many of these tackifiers. Upon aging and exposure to light, this discoloration can become even more pronounced, even with lighter colored grades of resin. (meth)acrylic-based adhesives without tackifiers typically have excellent aging properties.

Conventional tackified (meth)acrylic-based pressure-sensitive adhesives can also appear cloudy, demonstrating a loss in the characteristic transparency found in many conventional acrylate pressure-sensitive adhesive compositions. The cloudiness is an indication of limited or incomplete compatibility of the tackifier and the (meth)acrylic-based polymers. The reduced compatibility can lead to a degradation of adhesive properties on aging, as evidenced by a loss of tack or reduced peel adhesion. In some cases, the addition of a tackifier to an adhesive composition having (meth)acrylic-based monomers, polymers, oligomers, and any mixture thereof, can be clear and appear to be compatible. However, after removing the solvent, curing the adhesive, or on aging, the adhesive can become cloudy, indicating some incompatibility between the tackifier and (meth)acrylic-based polymer.

In addition to these losses in clarity and stability of tackified (meth)acrylic-based adhesives, other deleterious effects can be observed when tackifiers are present during bulk acrylic polymerization reactions. Depending on the structure of the tackifier, undesirable effects of adding a tackifier include the inhibition or retardation of the polymerization reaction and/or the alteration of the final polymer structure if the tackifier acts as a chain-transfer or chain-terminating agent. Such effects can adversely influence the performance and stability of acrylates polymerized in the presence of these tackifiers. Chain termination can also result in undesirably high residual volatile materials.

In many embodiments, the present disclosure provides tackified PSA compositions that overcome problems noted in the art. The tackifier is preferably selected from a material that is essentially free of any ethylenically or acetylenically unsaturated bonds. In certain embodiments a tackifier selected from a hydrogenated terpene resin, a hydrogenated rosin resin, an esterified rosin resin, an aliphatic petroleum resin, an aromatic petroleum resin, an alicyclic petroleum resin obtained by hydrogenating aromatic petroleum resins, and combinations thereof. Preferably, the tackifier used is selected from hydrogenated C9 petroleum resins such as but not limited to REGALREZ tackifiers (Eastman) or ARKON (Arakawa) tackifiers. Such "hydrophobic tackifiers" may be used in amounts of up to 150 parts, preferably 20 to 150 parts, more preferably 50 parts to 100 parts, of said tackifier, relative to 100 parts of said (meth)acrylate polymer.

The polymer compositions, particularly adhesives, of the present disclosure may be coated upon a variety of flexible and inflexible backing materials using, for example, conventional coating techniques to produce adhesive-coated materials. Flexible substrates are defined herein as any material that is conventionally utilized as a tape backing or may be of any other flexible material. Examples include, but are not limited to, plastic films such as polypropylene, polyethylene, polyvinyl chloride, polyester (polyethylene terephthalate), other polyesters (such as polyethylene naphthalate), polycarbonate, polymethyl(meth)acrylate (PMMA), cellulose acetate, cellulose triacetate, and ethyl cellulose. Foam backings may be used. Examples of inflexible substrates include, but are not limited to, metal, metallized polymeric film, indium tin oxide coated glass and polyester, PMMA plate, polycarbonate plate, glass, or ceramic sheet material. The adhesive-coated sheet materials may take the form of any article conventionally known to be utilized with adhesive compositions such as labels, tapes, signs, covers, marking indices, display components, touch panels, and the like. Flexible backing materials having microreplicated surfaces are also contemplated.

The above-described compositions are coated on a substrate using conventional coating techniques modified as appropriate to the particular substrate. For example, these compositions can be applied to a variety of solid substrates by methods such as roller coating, flow coating, dip coating, spin coating, spray coating knife coating, and die coating. These various methods of coating allow the compositions to be placed on the substrate at variable thicknesses thus allowing a wider range of use of the compositions. Coating thicknesses may vary, but coating thicknesses of 2-500 microns (dry thickness), preferably 25 to 250 microns, are contemplated.

The adhesives of the present disclosure are particularly useful for forming strong bonds to low surface energy (LSE) substrates. As used herein, low surface energy substrates are those having a surface energy of less than 45 dynes per centimeter, more typically less than 40 dynes per centimeter, and most typically less than 35 dynes per centimeter. Included among such materials are polypropylene, polyethylene (e.g., high density polyethylene or HDPE), polystyrene and poly (methyl methacrylate) (PMMA). Other substrates may also have properties of low surface energy due to a residue, such as an oil residue or a film, such as paint, being on the surface of the substrate. However, even though the present adhesive bonds well to low surface energy surfaces, the disclosure is not limited to being bonded to low surface energy substrates, as it has been found that the inventive adhesive can also bond well to higher surface energy substrates such as, for example, other plastics, ceramics (e.g., glass), and metals.

The substrate is selected depending on the particular application in which it is to be used. For example, the adhesive can be applied to sheeting products (e.g., decorative graphics and reflective products), label stock, and tape backings. Additionally, the adhesive may be applied directly onto a substrate such as an automotive panel, or a glass window so that another substrate or object can be attached to the panel or window.

The adhesive can also be provided in the form of a pressure-sensitive adhesive transfer tape in which at least one layer of the adhesive is disposed on a release liner for application to a permanent substrate at a later time. The adhesive can also be provided as a single coated or double coated tape in which the adhesive is disposed on a permanent backing. Backings can be made from plastics (e.g., polypropylene, including biaxially oriented polypropylene, vinyl, polyethylene, polyester such as polyethylene terephthalate), nonwovens (e.g., papers, cloths, nonwoven scrims), metal foils, foams (e.g., polyacrylic, polyethylene, polyurethane, neoprene), and the like. Foams are commercially available from various suppliers such as 3M Co., Voltek, Sekisui, and others. The foam may be formed as a coextruded sheet with the adhesive on one or both sides of the foam, or the adhesive may be laminated to it. When the adhesive is laminated to a foam, it may be desirable to treat the surface to improve the adhesion of the adhesive to the foam or to any of the other types of backings. Such treatments are typically selected based on the nature of the materials of the adhesive and of the foam or backing and include primers and surface modifications (e.g., corona treatment, surface abrasion). Additional tape constructions include those described in U.S. Pat. No. 5,602,221 (Bennett et al.).

For a single-sided tape, the side of the backing surface opposite that where the adhesive is disposed is typically coated with a suitable release material. Release materials are known and include materials such as, for example, silicone, polyethylene, polycarbamate, polyacrylics, and the like. For double coated tapes, another layer of adhesive is disposed on the backing surface opposite that where the adhesive of the disclosure is disposed. The other layer of adhesive can be different from the adhesive of the disclosure, e.g., a conventional (meth)acrylic ester PSA, or it can be the same adhesive as the disclosure, with the same or a different formulation. Double coated tapes are typically carried on a release liner.

Exemplary Embodiments

1. A pressure-sensitive adhesive composition comprising a (meth)acrylate polymer comprising interpolymerized monomers comprising at least three structural isomers of a secondary alkyl (meth)acrylate of Formula (I):

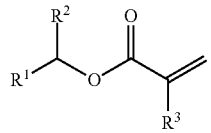

wherein:
$R^1$ and $R^2$ are each independently a $C_1$ to $C_{30}$ saturated linear alkyl group;
the sum of the number of carbons in $R^1$ and $R^2$ is 7 to 31; and
$R^3$ is H or $CH_3$.

2. A pressure-sensitive adhesive composition comprising a (meth)acrylate polymer comprising at least three structural isomers of a moiety of Formula (II):

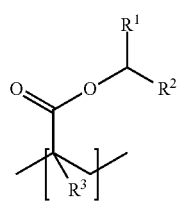

wherein:
$R^1$ and $R^2$ are each independently a $C_1$ to $C_{30}$ saturated linear alkyl group;
the sum of the number of carbons in $R^1$ and $R^2$ is 7 to 31; and
$R^3$ is H or $CH_3$.

3. The pressure-sensitive adhesive of embodiment 1 or embodiment 2 wherein $R^1$ and $R^2$ are each independently a $C_1$ to $C_{16}$ saturated linear alkyl and the sum of the number of carbons in $R^1$ and $R^2$ is 7 to 17.

4. The pressure-sensitive adhesive of embodiment 3 wherein $R^1$ and $R^2$ are each independently a $C_1$ to $C_6$ saturated linear alkyl and the sum of the number of carbons in $R^1$ and $R^2$ is 7 to 11.

5. The pressure-sensitive adhesive of embodiment 3 wherein $R^1$ and $R^2$ are each independently a $C_1$ to $C_{16}$ saturated linear alkyl and the sum of the number of carbons in $R^1$ and $R^2$ is 9 to 17.

6. The pressure-sensitive adhesive of any one of embodiments 1 through 5 wherein the polymer further comprises interpolymerized monomers comprising a (meth)acrylic acid ester of a $C_1$-$C_{32}$ alkanol.

7. The pressure-sensitive adhesive of any one of embodiments 1 through 6 wherein the polymer further comprises interpolymerized monomers comprising an acid-functional, ethylenically unsaturated monomer.

8. The pressure-sensitive adhesive of any one of embodiments 1 through 7 wherein the polymer further comprises interpolymerized monomers comprising a non-acid-functional, ethylenically unsaturated polar monomer.

9. The pressure-sensitive adhesive of any one of embodiments 1 through 8 wherein the polymer comprises:
a) 20 to 99.5 parts by weight of the at least three structural isomers of a secondary alkyl (meth)acrylate of Formula (I) or of a moiety of Formula (II);
b) 0 to 80 parts by weight of a (meth)acrylic acid ester of a $C_1$-$C_{32}$ alkanol;
c) 0.5 to 20 parts by weight of an acid-functional, ethylenically unsaturated monomer;
d) 0 to 10 parts by weight of a non-acid-functional, ethylenically unsaturated polar monomer;
e) 0 to 5 parts by weight of a vinyl monomer; and
f) 0 to 5 parts by weight of a multifunctional (meth)acrylate; based on 100 parts by weight total monomer.

10. The pressure-sensitive adhesive of any one of embodiments 1 through 9 further comprising a tackifier.

11. The pressure-sensitive adhesive of embodiment 10 comprising 20 to 150 parts of said tackifier, relative to 100 parts of the (meth)acrylate polymer.

12. The pressure-sensitive adhesive of embodiment 10 wherein said tackifier is a terpene resin, a hydrocarbon resin, a rosin resin, a petroleum resin, or combination thereof.

13. The pressure-sensitive adhesive of embodiment 12 wherein said tackifier is selected from a hydrogenated terpene resin, a hydrogenated rosin resin, an esterified rosin resin, an aliphatic petroleum resin, an alicyclic petroleum resin, and combinations thereof.

14. The pressure-sensitive adhesive of any one of embodiments 1 through 12, as dependent on embodiment 1, wherein the at least three structural isomers of an alkyl (meth)acrylate of Formula (I) are prepared by the reaction of (meth)acrylic acid with an olefin having a single unsaturation in the presence of a fluorinated sulfonic acid.

15. The pressure-sensitive adhesive of embodiment 14 wherein the at least three structural isomers of an alkyl (meth) acrylate of Formula (I) are prepared by the reaction of (meth) acrylic acid with an alpha-olefin in the presence of a fluorinated sulfonic acid.

16. The pressure-sensitive adhesive of any one of embodiments 1 through 15 which has a Tc of ≤0° C.

17. The pressure-sensitive adhesive of any one of embodiments 1 through 16, as dependent on embodiment 1, wherein the at least three structural isomers of an alkyl (meth)acrylate of Formula (I) are prepared by the reaction of (meth)acrylic acid with an olefin having a single unsaturation in a continuous process.

18. The pressure-sensitive adhesive of embodiment 17 wherein the continuous process uses a packed-bed reactor with a solid acid catalyst.

19. The pressure-sensitive adhesive of any one of embodiments 1 through 18, as dependent on embodiment 1, wherein the at least three structural isomers of an alkyl (meth)acrylate of Formula (I) comprise:
15-85 mole-% of a 2-alkyl (meth)acrylate isomer;
5-50 mole-% of a 3-alkyl (meth)acrylate isomer;
0.5-40 mole-% of a 4-alkyl (meth)acrylate isomer; and
0-50 mole-% of at least one of a 5- through 15-alkyl (meth) acrylate isomer;

wherein the mole percentages are based on the total moles of (meth)acrylate isomers used to make the polymer.

20. A pressure-sensitive adhesive article comprising a coating of the adhesive of any one of embodiments 1 through 19 on a backing.

21. A method of making a mixture of structural isomers of a secondary alkyl (meth)acrylate of Formula (I):

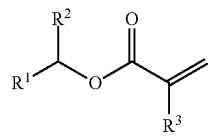

(I)

wherein:
$R^1$ and $R^2$ are each independently a $C_1$ to $C_{30}$ saturated linear alkyl group;
the sum of the number of carbons in $R^1$ and $R^2$ is 7 to 31; and
$R^3$ is H or $CH_3$;
wherein the method comprises reacting (meth)acrylic acid with an olefin having a single unsaturation in the presence of a fluorinated sulfonic acid.

22. The method of embodiment 21 wherein the fluorinated sulfonic acid has the formula: $R^4$—$(CF_2$—$SO_3H)_n$, wherein n is one or two, and $R^4$ is a fluorine, a carboxylic acid group, a $C_1$-$C_{12}$ alkyl group, a $C_1$-$C_{12}$ alkylene group, a fluorinated $C_1$-$C_{12}$ alkyl group, a fluorinated $C_1$-$C_{12}$ alkylene group, a perfluoroether $C_1$-$C_{12}$ heteroalkyl group, or a perfluoroether $C_1$-$C_{12}$ heteroalkylene group.

23. The method of embodiment 21 or 22 wherein the fluorinated sulfonic acid is trifluoromethanesulfonic acid.

24. The method of embodiment 21 or 22 wherein the fluorinated sulfonic acid is a sulfonated tetrafluoroethylene based fluoropolymer-copolymer.

25. The method of embodiment 21 or 22 wherein the fluorinated sulfonic acid is nonafluorobutanesulfonic acid.

26. The method of any one of embodiments 21 through 25 wherein reacting (meth)acrylic acid with an olefin in the presence of a fluorinated sulfonic acid occurs at a temperature of 40° C. to 150° C.

27. The method of any one of embodiments 21 through 26 wherein reacting (meth)acrylic acid with an olefin occurs in the presence of a 0.01 mole percent to 10 mole percent acid fluorinated sulfonic acid.

28. The method of any one of embodiments 21 through 27 wherein reacting (meth)acrylic acid with an olefin in the presence of a fluorinated sulfonic acid reaches equilibrium within 5 minutes to 48 hours.

29. A method of making a mixture of structural isomers of a secondary alkyl (meth)acrylate of Formula (I):

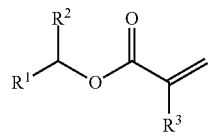

(I)

wherein:
$R^1$ and $R^2$ are each independently a $C_1$ to $C_{30}$ saturated linear alkyl group;

the sum of the number of carbons in $R^1$ and $R^2$ is 7 to 31; and
$R^3$ is H or $CH_3$;
wherein the method involves reacting (meth)acrylic acid with an olefin having a single unsaturation, wherein the olefin has been pre-treated with an acid to give a mixture of olefin isomers.

30. The method of embodiment 29 wherein reacting the (meth)acrylic acid with an olefin having a single unsaturation occurs in a continuous process.

31. The method of embodiment 30 wherein the continuous process uses a packed-bed reactor with a solid acid catalyst.

32. The method of any one of embodiments 21 through 31 wherein the olefin having a single unsaturation is an alpha-olefin.

33. The method of any one of embodiments 21 through 31 wherein the olefin is 1-octene, 2-octene, 3-octene, 4-octene, 1-nonene, 2-nonene, 3-nonene, 4-nonene, 1-decene, 5-decene, 1-undecene, 1-dodecene, 1-tridecene, 1-tetradecene, 7-tetradecene, 1-pentadecene, 1-hexadecene, 1-heptadecene, 1-octadecene, 1-nonadecene, 1-eicosene, 9-heneicosene, 1-docosene, 9-tricosene, 1-tetracosene, 1-octacosene, 1-triacontene, or mixtures thereof.

34. The method of any one of embodiments 21 through 33 wherein $R^1$ and $R^2$ are each independently a $C_1$ to $C_{16}$ saturated alkyl and the sum of the number of carbons in $R^1$ and $R^2$ is 7 to 17.

35. The method of embodiment 34 wherein $R^1$ and $R^2$ are each independently a $C_1$ to $C_6$ saturated alkyl and the sum of the number of carbons in $R^1$ and $R^2$ is 7 to 11.

36. The method of embodiment 34 wherein $R^1$ and $R^2$ are each independently a $C_1$ to $C_{16}$ saturated linear alkyl and the sum of the number of carbons in $R^1$ and $R^2$ is 9 to 17.

37. The method of any one of embodiments 21 through 36 wherein the mixture of structural isomers of an alkyl (meth)acrylate of Formula (I) comprise:
15-85 mole-% of a 2-alkyl (meth)acrylate isomer;
5-50 mole-% of a 3-alkyl (meth)acrylate isomer;
0.5-40 mole-% of a 4-alkyl (meth)acrylate isomer; and
0-40 mole-% of at least one of a 5- through 15-alkyl (meth)acrylate isomer;
wherein the mole percentages are based on the total moles of (meth)acrylate isomers.

38. A mixture of structural isomers of a secondary alkyl (meth)acrylate of Formula (I):

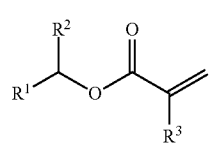

(I)

wherein:
$R^1$ and $R^2$ are each independently a $C_1$ to $C_{30}$ saturated linear alkyl group;
the sum of the number of carbons in $R^1$ and $R^2$ is 7 to 31; and
$R^3$ is H or $CH_3$;
wherein the 2-alkyl (meth)acrylate isomer is less than 35 mole-% of the total mixture of alkyl (meth)acrylate isomers.

39. A polymer made from the mixture of embodiment 38.

40. A (meth)acrylate polymer comprising interpolymerized monomers comprising:

a) at least three structural isomers of a secondary alkyl (meth)acrylate of Formula (I):

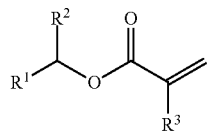

wherein:

$R^1$ and $R^2$ are each independently a $C_1$ to $C_{30}$ saturated linear alkyl group;

the sum of the number of carbons in $R^1$ and $R^2$ is 7 to 31; and $R^3$ is H or $CH_3$; and b) at least one monomer selected from:
i) a (meth)acrylic acid ester of a $C_1$-$C_{32}$ alkanol;
ii) an acid-functional, ethylenically unsaturated monomer;
iii) a non-acid-functional, ethylenically unsaturated polar monomer;
iv) a vinyl monomer; and
v) a multifunctional (meth)acrylate.

41. The polymer of embodiment 40 wherein $R^1$ and $R^2$ are each independently a $C_1$ to $C_{16}$ saturated linear alkyl and the sum of the number of carbons in $R^1$ and $R^2$ is 7 to 17.

42. The polymer of embodiment 41 wherein $R^1$ and $R^2$ are each independently a $C_1$ to $C_6$ saturated linear alkyl and the sum of the number of carbons in $R^1$ and $R^2$ is 7 to 11.

43. The polymer of embodiment 41 wherein $R^1$ and $R^2$ are each independently a $C_1$ to $C_{16}$ saturated linear alkyl and the sum of the number of carbons in $R^1$ and $R^2$ is 9 to 17.

44. The (meth)acrylate polymer of any one of embodiments 40 through 43 wherein the interpolymerized monomers comprise at least one monomer selected from a (meth)acrylic acid ester of a $C_1$-$C_{32}$ alkanol, an acid-functional, ethylenically unsaturated monomer, a non-acid-functional, ethylenically unsaturated polar monomer, and a mixture thereof.

45. The (meth)acrylate polymer of embodiment 44 wherein the interpolymerized monomers comprise an acid-functional, ethylenically unsaturated monomer.

46. The (meth)acrylate polymer of embodiment 45 wherein the interpolymerized monomers comprise:

a) 20 to 99.5 parts by weight of the at least three structural isomers of a secondary alkyl (meth)acrylate of Formula (I); and b) 0 to 80 parts by weight of a (meth)acrylic acid ester of a $C_1$-$C_{32}$ alkanol;

c) 0.5 to 20 parts by weight of an acid-functional, ethylenically unsaturated monomer;

d) 0 to 10 parts by weight of a non-acid-functional, ethylenically unsaturated polar monomer;

e) 0 to 5 parts by weight of a vinyl monomer; and f) 0 to 5 parts by weight of a multifunctional (meth)acrylate; based on 100 parts by weight total monomer.

EXAMPLES

Objects and advantages of this disclosure are further illustrated by the following examples, but the particular materials and amounts thereof recited in these examples, as well as other conditions and details, should not be construed to unduly limit this disclosure. The materials used in the following examples were purchased from Alfa Aesar (Ward Hill, Mass.) (where noted) or from Sigma-Aldrich Company (St. Louis, Mo.) unless otherwise stated.

Test Method 1: Differential Scanning Calorimetric (DSC) Analysis of Monomers and Homopolymer Films Approximately 10 mg of a given monomer was placed in an individual standard aluminum DSC pans (Thermal Analysis T080715), which was then placed in the auto sampler of a differential scanning calorimeter (DSC, TA Instruments, New Castle, Del.). For each sample analysis, the pan was individually placed on one of the differential posts in the DSC's enclosed cell along with an empty reference pan on the opposite post. Temperature was raised to 55° C. and held for 10 minutes to thermally anneal the sample which was then cycled between −95° C. and 55° C. twice at 3° C./min. Transitions such as the crystallinity temperature (Tc), melting temperature (Tm), and glass transition temperature (Tg) were identified as their respective peaks in the scanning profile of heat flow vs. temperature. Typically, crystallization and melting transitions show up as positive and negative heat flow peaks as the sample is cooled and heated respectively. Conversely a glass transition is generally represented by a shift in the profile shape upon heating because the heat capacity of the sample after passing through the glass transition temperature is altered. The glass transition temperature was recorded at the inflection point of the curve associated with this shift in heat flow profile.

DSC analysis as described above was repeated for the homopolymer of each of the monomers. To generate homopolymer samples 1 g of each acrylic monomer was mixed with 1 wt % IRGACURE 651 (Ciba Spec. Chem.—a Division of BASF Corp., Florham Park, N.J.) for 1 hour in an amber vial with magnetic stirring. Using a syringe, 10-20 mg of formulated monomer was then added to the DSC pan and mass was recorded. The pan was then placed in a small nitrogen glove box with glass top, purged with nitrogen for 5 minutes, and then exposed to UV irradiation (365 nm, approximately 5 mW/cm$^2$) for 10 minutes. The DSC pan containing the homopolymer was then loaded into the DSC and analyzed following the same procedure used for each monomer sample, as described above.

Test Method 2: Visual Analysis of Adhesive Formulated Films

Tackified and polymerized adhesive films were characterized for clarity by classifying the adhesive film as clear, translucent, or opaque.

Test Method 3: Peel Adhesion Strength

Peel adhesion is the force required to remove a coated flexible sheet material from a test panel measured at a specific angle and rate of removal. In the examples of this disclosure, the force is expressed in Newtons per width of coated sheet (N/dm). For each test, a 12.7 millimeters (mm) width of the adhesive coated sheet material approximately 10-12 centimeters (cm) long was cut and the release layer peeled away from the coated adhesive. The adhesive strip was then applied to the clean face of the test panel. A heavy rubber roller was used to apply the strip to the panel. The stainless steel plate was then affixed to the platform of the peel tester (slip/peel tester model 3M90, Instrumentors Inc., Strongsville, Ohio) which is mechanized to move at a controlled rate (30.5 cm/min) away from the load cell. The free end of the coated strip was doubled back so that the angel of removal was 180 degrees. The free end of the adhesive coated sheet was attached to the horizontal arm of the adhesion tester. The peel test was started soon after the adhesive was applied to the substrate without allowing for an induction time for adhesion to build. The load was read during the test as an average of the peak maximum and minimum forces during the peel. Three peel tests were run for each sample and averaged to yield the peel adhesion value.

Peel adhesion was measured for each sample using test panels of both standard stainless steel and high density polyethylene (HDPE, International Plastics—Edina, Minn.).

Test Method 4: High Temperature Shear Strength

Shear strength of an adhesive material is directly related to the internal strength or cohesiveness of the sample and is typically quantified by the amount of force required to pull an adhesive strip from a standard flat surface to which the sample has been affixed. Specifically, shear strength is measured in terms of the time required to pull a defined area of adhesive coated backing material from a stainless steel test panel under the stress of a constant or static load parallel to the test panel.

Shear tests were conducted using PET substrate coated with approximately a 0.08 mm thick adhesive coating. For each test, a cut adhesive strip was applied to a clean stainless steel panel such that a 25.4 mm by 12.7 mm portion of each strip was in firm contact with the panel and one end portion of each strip was free. The panel bearing the adhesive strip was held in a rack such that the panel formed a 180 degree angle with the extended free end, which was then tensioned by applying a one kilogram hanging weight. The rack was enclosed in a 70° C. oven and the time elapsed for the test specimen to separate from the test panel was recorded as the shear strength in minutes. Two shear tests were performed for each sample adhesive and the average was reported.

Test Method 5: Determination of Acrylate Isomer Distribution by Quantitative C13 NMR A solution of 150 mg of the alkyl acrylate, 10-15 mg of chromium(III) acetylacetonate, in 1.2 grams of deuterochloroform is prepared and filtered into a 5 mm NMR tube. A quantitative C13 NMR was obtained on a 500 MHz system Bruker Avance 3 console with standard gated decoupled carbon parameters using a 10 second delay and 90 degree carbon pulse. The absorption for the methine carbon (point of attachment for the acrylate ester) was integrated and compared for 2, 3, 4 and 5 and higher isomers. The results are presented below in Table 1.

Example 1

Octel Acrylate Isomer Blend from 1-Octene

To 200.0 grams (g) (1.782 moles, 1 equivalent (eq)) of 1-octene at 50° C. was added a solution of 145.1 g (2.014 moles, 1.13 eq) of acrylic acid (Alfa Aesar) and 5.349 g (0.03564 moles, 0.02 eq) of trifluoromethanesulfonic acid (Alfa Aesar). After 10 minutes at 50° C., the mixture was heated to 70° C. and exothermed to 90° C. The mixture cooled to 70° C. in one hour and remained at 70° C. for 15 hours. To the reaction mixture was added 411.3 g of a 9.1 wt-% solution (0.4456 mole, 0.25 eq) of sodium bicarbonate (saturated aqueous solution). The mixture was stirred for 30 minutes and then allowed to phase separate. Additional charge of 411.3 g of a 9.1 wt-% solution (0.4456 mole, 0.25 eq) of sodium bicarbonate (saturated aqueous solution) was added and stirred for 30 minutes. To the organic phase was added 300 mg of phenothiazine and 100 mg of (methoxyhydroquinone) (MEHQ) (Alfa Aesar) and the mixture was distilled. The first fraction was octene. The second fraction (boiling point 104° C., reduced pressure 1-10 ton) was octyl acrylate (57.6% yield). To this product was added 100 parts per million (ppm) of monomethyl ether hydroquinone (MEHQ).

Example 2

Octyl Acrylate Using an Excess of Acrylic Acid

To 10.0 g (0.0891 mole, 1 eq) of 1-octene and 0.00679 g of copper(II) chloride dihydrate was added a mixture of 19.2 g (0.267 mole, 3 eq) of acrylic acid and 0.802 g (0.00534 mole, 0.06 eq) of trifluoromethanesulfonic acid. The mixture was heated to 40° C. for 30 minutes and then to 70° C. for 15 hours. This gave an 83% conversion to the desired acrylate based on 1-octene consumed.

Example 3

Octel Acrylate from Pre-Isomerized Octene

To 40.0 g (356 millimoles (mmoles), 4 eq) of 1-octene was added 0.535 g (3.56 mmoles, 0.04 eq) of trifluoromethanesulfonic acid at room temperature, and then the mixture was heated to 70° C. for 20 hours. Acrylic acid was added (6.42 g, 89.1 mmoles, 1 eq) to the reaction mixture, which was kept at 80° C. for 18 hours to give 88% conversion to the desired acrylate based on acrylic acid consumed.

Example 4

Octyl Acrylate from Pre-Isomerized Octene

A mixture of 30.0 g (267 mmoles, 3 eq) of 1-octene and 0.802 g (5.35 mmoles, 0.06 eq) of trifluoromethanesulfonic acid was heated to 90° C. for 150 minutes. NMR indicted there was less than 1.0% 1-octene in the reaction mixture. To this reaction mixture was added 6.42 g (89.1 mmoles, 1 eq) of acrylic acid and the mixture was heated to 90° C. for 5 hours. The mixture was cooled to room temperature, and 36.2 g of a saturated solution of sodium bicarbonate in water (8.28 wt-%, 35.6 mmoles, 0.4 eq) was added. The reaction mixture was stirred for 30 minutes and was allowed to phase separate. The bottom aqueous phase was removed. The residue was distilled to isolate the octene. The pot residue was distilled (0.75 torr, 73-76° C.) to give 4.61 grams of octyl acrylate product. The yield was 75% based on acrylic acid consumed.

Example 5

Octyl Acrylate Using a Sulfonated Tetrafluoroethylene Based Fluoropolymer-Copolymer A mixture of 3.00 g (26.7 mmoles, 3 eq) of 1-octene and 0.6421 g (8.91 mmoles, 1 eq) of acrylic acid was stirred with 0.2220 g (0.202 mmole, 0.023 eq) of NAFION® NR50 (a sulfonated tetrafluoroethylene based fluoropolymer-copolymer obtained from Alfa Aesar) and heated to 115° C. for 18 hours. NMR indicated 66% conversion to octyl acrylate based on acrylic acid consumed.

Example 6

Octyl Acrylate Using Nonafluorobutanesulfonic Acid

A mixture of 15.0 g (134 mmoles, 3 eq) of 1-octene, 3.21 g (44.6 mmoles, 1 eq) of acrylic acid, 0.401 g (1.34 mmoles, 0.03 eq) of nonafluorobutane-1-sulfonic acid (TCI America, Portland, Oreg.), 0.00277 g of MEHQ and 0.0034 g of copper (II) chloride dihydrate was heated to 90° C. for 2 hours. NMR indicated 86% conversion to octyl acrylate based on acrylic acid consumed.

Example 7

Octyl Acrylate, Using 0.006 Eq of Trifluoromethanesulfonic Acid

A mixture of 15.0 g (134 mmoles, 3 eq) of 1-octene, 3.21 g (44.6 mmoles, 1 eq) of acrylic acid, 0.0401 g (0.267 mmoles, 0.006 eq) of trifluoromethanesulfonic acid, 0.0277 g of MEHQ and 0.0034 g of copper(II) chloride dihydrate was heated at 105° C. for 20 hours. NMR indicated 83% conversion to octyl acrylate based on acrylic acid consumed.

Example 8

Octyl Methacrylate

To 30.0 g (267 mmoles, 3 eq) of 1-octene was added 0.802 g (5.35 mmoles, 0.06 eq) of trifluoromethanesulfonic acid followed by 7.67 g (89.1 mmoles, 1 eq) of methacrylic acid. This mixture was heated to 90° C. for 6 hours. By NMR, the yield was 81% based on acrylic acid consumed. To the reaction mixture was added 36.16 g of a saturated solution of sodium bicarbonate in water (8.28 wt-%, 35.6 mmoles, 0.4 eq) and the mixture was stirred at room temperature for 1 hour. The aqueous phase was removed and the residue was distilled at 25° C./10-20 torr. The receiver was cooled with dry ice to trap the octene. This gave 14 grams of recovered octene. The product was distilled at 103° C./1.0 torr to give 14.7 g of octyl methacrylate (83.2% yield based on acrylic acid consumed).

Example 9

Dodecyl Acrylate Isomer Blend from 1-Dodecene

To 20.00 g (0.1188 mole, 1 eq) of 1-dodecene (Alfa Aesar) at 50° C. was added a solution of 9.675 g (0.1343 mole, 1.13 eq) of acrylic acid and 0.3567 g (0.002376 mole, 0.02 eq) of trifluoromethanesulfonic acid. The addition was performed slowly in order to prevent the reaction temperature from rising above 52° C. The mixture was then heated to 70° C. for 18 hours. The reaction mixture was cooled to room temperature, washed with saturated sodium bicarbonate, and extracted with ethyl acetate. The organic layer was concentrated and distilled. The first fraction was a mixture of 2-, 3-, 4-, 5-, and 6-dodecene. The second fraction (bp 112-120° C. reduced pressure) was a mixture of dodecyl acrylates totaling 11.60 g (41% yield). To this product was added 100 ppm of MEHQ.

Example 10

Tetradecyl Acrylate Isomer Blend from 1-Tetradecene

To 100.0 g (0.5092 mole, 1 eq) of 1-tetradecene (Alfa Aesar) at 50° C. was added a solution of 41.46 g (0.5754 mole, 1.13 eq) of acrylic acid and 1.528 g (0.01018 moles, 0.02 eq) of trifluoromethanesulfonic acid. The addition was performed slowly in order to prevent the reaction temperature from rising above 70° C. The mixture was then heated at 70° C. for 16 hours. The mixture was cooled to room temperature, poured into water, and extracted with ethyl acetate. The ethyl acetate layer was washed well with saturated aqueous sodium bicarbonate, dried with MgSO$_4$, and concentrated in vacuo, to give 116 grams of crude product. A sample of the crude reaction mixture (100.00 g) was distilled under reduced pressure. The tetradecyl acrylate product fraction (51.98 g) was collected as a slight yellow oil boiling at 70-85° C. at 40 mTorr.

Example 11

Hexadecyl Acrylate Isomer Blend from 1-Hexadecene

To 50.00 g (0.2228 mole, 1 eq) of 1-hexadecene (Alfa Aesar) at 50° C. was added a solution of 18.14 g (0.2517 mole, 1.13 eq) of acrylic acid and 0.6687 g (0.004456 mole, 0.02 eq) of trifluoromethanesulfonic acid. The addition was performed slowly in order to prevent the reaction temperature from rising above 70° C. The mixture was then heated to 70° C. for 18 hours. The mixture was poured into water, and extracted with ethyl acetate. The ethyl acetate layer was washed well with saturated aqueous sodium bicarbonate, dried with MgSO$_4$ and concentrated in vacuo to give 54 grams of crude product. To some of the mixture (45 g) was added phenothiazine (0.3 g) and the mixture was distilled under reduced pressure. A liquid mixture of alkenes distilled at 50° C. at 0.2 mTorr (20.30 g). The residual oil that did not distill was diluted with hexane (30 mL) and filtered through a bed of neutral alumina, which was then eluted with hexane (250 mL). The mixture was then concentrated under vacuum to give the hexadecyl acrylate product as a yellow oil (21.50 g).

Example 12

Octadecyl Acrylate Isomer Blend from 1-Octadecene

To 15.00 g (0.05941 mole, 1 eq) of 1-octadecene (Alfa Aesar) at 50° C. was added a solution of 4.838 g (0.06713 mole, 1.13 eq) of acrylic acid and 0.1783 g (0.001188 mole, 0.02 eq) of trifluoromethanesulfonic acid. The reaction was heated to 90° C. for 18 hours. The mixture was poured into water, and extracted with ethyl acetate. The ethyl acetate layer was washed well with saturated aqueous sodium bicarbonate, dried with MgSO$_4$, and concentrated in vacuo to give 11.86 grams of crude product. A portion of the crude reaction mixture (6.00 g) was purified by column chromatography over silica gel using a solvent mixture of 10 vol-% ethyl acetate in hexane. The octadecyl acrylate product was isolated as a colorless oil (3.16 g).

Example 13

Dodecyl Acrylate Isomer Blend from Pre-Isomerized 1-Dodecene

To 40.0 grams (g) (0.238 mole, 1 eq) of 1-dodecene was added 2.675 g (0.0178 mole, 0.075 eq) of trifluoromethanesulfonic acid. This mixture was heated to 50° C. for 3 hours. To this was added 19.35 g (0.2685 mole, 1.13 eq) of acrylic acid and the mixture was heated at 50° C. for 3 hours. The reaction mixture was diluted with ethyl acetate (100 mL) and washed two times with 54.85 g of a 9.1 wt-% solution of sodium bicarbonate (saturated aqueous solution). Phenothiazine (0.04 g) was added and the mixture concentrated in vacuo. The mixture was distilled under vacuum (approximately 300 mtorr). A first fraction was collected at 40° C. and contained mostly dodecene isomers. A second fraction was collected at 98-100° C. (at 300 mtorr) and contained a mixture of dodecyl acrylate isomers.

Example 14

Octyl Acrylate Isomer Blend from 1-Octene

A 0.5-inch (in) inside diameter (I.D.) by 18-in length stainless steel reactor tube was charged with 57 g of AMBERLYST 36 Dry catalyst material (a sulfonated styrene divinylbenzene copolymer). A 1:1 molar ratio of pre-mixed 1-octene:acrylic acid (acrylic acid containing 200 ppm MEHQ by weight) was fed to the reactor at 1 milliliter per minute (mL min$^{-1}$) total flow rate (0.00443 mole per minute (mol min$^{-1}$) or 0.49765 gram per minute (g min$^{-1}$) of 1-octene, 0.00443 mol min$^{-1}$ or 0.31950 g min$^{-1}$ of acrylic acid) corresponding to a reactant residence time of approximately 25 minutes (min). Reactor temperature and pressure were held constant at 60° C. and 0.35 MPa, respectively. After allowing three residence times to reach steady state, product was collected for analysis and found to contain primarily a mixture of acrylic acid, octene isomers, and octyl acrylate isomers.

The crude reaction mixture was dissolved in ethyl acetate and washed with a saturated solution of sodium bicarbonate and then concentrated under reduced pressure (approximately 10 torr). The residue was distilled at approximately 1 torr to give octyl acrylate (boiling point (bp) 80-84° C.).

Example 15-16

Decyl Acrylate Isomer Blend From 1-Decene

A 0.5-in I.D. by 18-in length stainless steel reactor tube was charged with 57 g of AMBERLYST 36 Dry catalyst material (a sulfonated styrene divinylbenzene copolymer). A 1:1 molar ratio of pre-mixed 1-decene:acrylic acid (acrylic acid containing 200 ppm MEHQ by weight) was fed to the reactor at 1 mL min$^{-1}$ total flow rate (0.00387 mol min$^{-1}$ or 0.54397 g min$^{-1}$ of 1-decene, 0.00387 mol min$^{-1}$ or 0.27945 g min$^{-1}$ of acrylic acid) corresponding to a reactant residence time of approximately 25 min Reactor temperature was held constant at 70° C. for Example 15 and at 90° C. for Example 16. After allowing three residence times to reach steady state, product was collected for analysis and found to contain primarily a mixture of acrylic acid, decene isomers, and decyl acrylate isomers.

The crude reaction mixture (342.31 g for Example 15, 350.39 g for Example 16) was diluted with ethyl acetate (300 mL). The mixture was washed with saturated aqueous sodium bicarbonate until the aqueous layer was basic. The organic layer was concentrated in vacuo to give the crude product. Bis(1-oxyl-2,2,6,6-tetramethylpiperidin-4-yl) isophthalate (0.1 g, can be prepared according to Example 14 in U.S. Pat. No. 5,574,163) was added and the mixture was distilled under reduced pressure. The first fraction consisting primarily of alkene was collected at 38-40° C. at 1 mmHg (65.00 g for Example 15, 75.00 g for Example 16). A second fraction containing the acrylate product was collected as a colorless oil at 75-85° C. at 0.3 mmHg (177.16 g for Example 15, and 157.31 g for Example 16).

Example 17-18

Dodecyl Acrylate Isomer Blend from 1-Dodecene

A 0.5-in I.D. by 18-in length stainless steel reactor tube was charged with 57 g of AMBERLYST 36 Dry catalyst material (a sulfonated styrene divinylbenzene copolymer). A 1:1 molar ratio of pre-mixed 1-dodecene:acrylic acid (acrylic acid containing 200 ppm MEHQ by weight) was fed to the reactor at 1 mL min$^{-1}$ total flow rate (0.00345 mol min$^{-1}$ or 0.58151 g min$^{-1}$ of 1-dodecene, 0.00345 mol min$^{-1}$ or 0.24895 g min$^{-1}$ of acrylic acid) corresponding to a reactant residence time of approximately 25 min Reactor temperature was held constant at 70° C. for Example 17 and 90° C. for Example 18. After allowing three residence times to reach steady state, product was collected for analysis and found to contain primarily a mixture of acrylic acid, dodecene isomers, and dodecyl acrylate isomers.

The crude reaction mixture (334.85 g for Example 17, 339.38 g for Example 18) was diluted with ethyl acetate (300 mL). The mixture was washed with saturated aqueous sodium bicarbonate until the aqueous layer was basic. The organic layer was concentrated in vacuo to give the crude product. Bis(1-oxyl-2,2,6,6-tetramethylpiperidin-4-yl) isophthalate (0.1 g) was added and the mixture was distilled under reduced pressure. The first fraction consisting primarily of alkene was collected at 60-70° C. at 0.5 mmHg (166.88 g for Example 17, 135.44 g for Example 18). A second fraction containing the acrylate product was collected as a colorless oil at 95-105° C. at 0.3 mmHg (105.32 g for Example 17, and 125.35 g for Example 18).

Example 19-20

Tetradecyl Acrylate Isomer Blend from 1-Tetradecene

A 0.5-in I.D. by 18-in length stainless steel reactor tube was charged with 57 g of AMBERLYST 36 Dry catalyst material (a sulfonated styrene divinylbenzene copolymer). A 1:1 molar ratio of pre-mixed 1-tetradecene:acrylic acid (acrylic acid containing 200 ppm MEHQ by weight) was fed to the reactor at 1 mL min$^{-1}$ total flow rate (0.00311 mol min$^{-1}$ or 0.60996 g min$^{-1}$ of 1-tetradecene, 0.00311 mol min$^{-1}$ or 0.22382 g min$^{-1}$ of acrylic acid) corresponding to a reactant residence time of approximately 25 min Reactor temperature was held constant at 70° C. for Example 19 and at 90° C. for Example 20. After allowing three residence times to reach steady state, product was collected for analysis and found to contain primarily a mixture of acrylic acid, tetradecene isomers, and tetradecyl acrylate isomers.

The crude reaction mixture (339.88 g for Example 19, 369.58 g for Example 20) was diluted with ethyl acetate (300 mL). The mixture was washed with saturated aqueous sodium bicarbonate until the aqueous layer was basic. The organic layer was concentrated in vacuo to give the crude product. Bis(1-oxyl-2,2,6,6-tetramethylpiperidin-4-yl) isophthalate (0.1 g) was added and the mixture was distilled under reduced pressure. The first fraction consisting primarily of alkene was collected at 80-90° C. at 0.2 mmHg (191.00 g for Example 19, 167.04 g for Example 20). A second fraction containing the acrylate product was collected as a colorless oil at 120-127° C. at 0.2 mmHg (50.55 g for Example 19, and 98.66 g for Example 20).

Example 21-22

Hexadecyl Acrylate Isomer Blend from 1-Hexadecene

A 0.5-in I.D. by 18-in length stainless steel reactor tube was charged with 57 g of AMBERLYST 36 Dry catalyst material (a sulfonated styrene divinylbenzene copolymer). A 1:1 molar ratio of pre-mixed 1-hexadecene:acrylic acid (acrylic acid containing 200 ppm MEHQ by weight) was fed to the reactor at 1 mL min$^{-1}$ total flow rate (0.00282 mol min$^{-1}$ or 0.63316 g min$^{-1}$ of 1-hexadecene, 0.00282 mol min$^{-1}$ or 0.20329 g min$^{-1}$ of acrylic acid) corresponding to a reactant residence time of approximately 25 min Reactor temperature was held constant at 70° C. for Example 21 and at 90° C. for Example 22. After allowing three residence times to reach steady state, product was collected for analysis and found to contain primarily a mixture of acrylic acid, hexadecene isomers, and hexadecyl acrylate isomers.

The crude reaction mixture (371.63 g for Example 21, 345.72 g for Example 22) was diluted with ethyl acetate (300 mL). The mixture was washed with saturated aqueous sodium bicarbonate until the aqueous layer was basic. The organic layer was concentrated in vacuo to give the crude product. Bis(1-oxyl-2,2,6,6-tetramethylpiperidin-4-yl) isophthalate (0.1 g) was added and the mixture was distilled under reduced pressure. A fraction consisting primarily of alkene was collected at 95-105° C. at 0.2 mmHg (237.55 g for Example 21, 180.00 g for Example 22). The residual oil that did not distill was diluted with hexane (50 mL) and filtered through a bed of neutral alumina, which was then eluted with hexane (300 mL). The mixture was then concentrated under vacuum to give the product as a colorless oil (16.26 g for Example 21, and 54.43 g for Example 22).

Example 23

Dodecyl Acrylate Isomer Blend from Dodecene Isomer Blend

A 0.5-in I.D. by 18-in length stainless steel reactor tube was charged with 42 g of AMBERLYST 15 Dry catalyst material (a sulfonated styrene divinylbenzene copolymer). In step 1,1-dodecene was fed to the reactor for isomerization at 1 mL min$^{-1}$ total flow rate corresponding to a reactant residence time of approximately 25 min. Reactor temperature and pressure were held constant at 100° C. and 0.35 MPa, respectively. After allowing three residence times to reach steady state, product collection was initiated. In step 2, the isomerized olefin product from step 1 was mixed in a 1:1 molar ratio with acrylic acid (acrylic acid containing 200 ppm MEHQ by weight) and fed to the same reactor configuration and catalyst (fresh catalyst bed) at 1 mL min$^{-1}$ total flow rate (0.00345 mol min$^{-1}$ or 0.58151 g min$^{-1}$ of dodecene isomers, 0.00345 mol min$^{-1}$ or 0.24895 g min$^{-1}$ of acrylic acid) corresponding to a reactant residence time of approximately 25 min. Reactor temperature and pressure were held constant at 80° C. and 0.35 MPa, respectively. After allowing three residence times to reach steady state, product was collected for analysis and found to contain primarily a mixture of acrylic acid, dodecene isomers, and dodecyl acrylate isomers.

The crude reaction mixture (243.40 g) was diluted with ethyl acetate (300 mL). The mixture was washed with saturated aqueous sodium bicarbonate until the aqueous layer was basic. The organic layer was concentrated in vacuo to give the crude product. Bis(1-oxyl-2,2,6,6-tetramethylpiperidin-4-yl) isophthalate (0.02 g) was added and the mixture was distilled under reduced pressure. The first fraction consisting primarily of alkene was collected at 60-70° C. at 0.5 mmHg (118.80 g). A second fraction containing the acrylate product was collected as a colorless oil at 95-105° C. at 0.3 mmHg (44.55 g).

Example 24

Tetradecyl Acrylate Isomer Blend from Tetradecene Isomer Blend

A 0.5-in I.D. by 18-in length stainless steel reactor tube was charged with 42 g of AMBERLYST 15 Dry catalyst material (a sulfonated styrene divinylbenzene copolymer). In step 1,1-tetradecene was fed to the reactor for isomerization at 1 mL min$^{-1}$ total flow rate corresponding to a reactant residence time of approximately 25 min. Reactor temperature and pressure were held constant at 100° C. and 0.35 MPa, respectively. After allowing three residence times to reach steady state, product collection was initiated. In step 2, the isomerized olefin product from step 1 was mixed in a 1:1 molar ratio with acrylic acid (acrylic acid containing 200 ppm MEHQ) and fed to the same reactor configuration and catalyst (fresh catalyst bed) at 1 mL min$^{-1}$ total flow rate (0.00311 mol min$^{-1}$ or 0.60996 g min$^{-1}$ of tetradecene isomers, 0.00311 mol min$^{-1}$ or 0.22382 g min$^{-1}$ of acrylic acid) corresponding to a reactant residence time of approximately 25 min. Reactor temperature and pressure were held constant at 80° C. and 0.35 MPa, respectively. After allowing three residence times to reach steady state, product was collected for analysis and found to contain primarily a mixture of acrylic acid, tetradecene isomers, and tetradecyl acrylate isomers.

The crude reaction mixture (241.38 g) was diluted with ethyl acetate (300 mL). The mixture was washed with saturated aqueous sodium bicarbonate until the aqueous layer was basic. The organic layer was concentrated in vacuo to give the crude product. Bis(1-oxyl-2,2,6,6-tetramethylpiperidin-4-yl) isophthalate (0.05 g) was added and the mixture was distilled under reduced pressure. The first fraction consisting primarily of alkene was collected at 80-90° C. at 0.4 mmHg (131.28 g). A second fraction containing a mixture of the acrylate product and alkenes was collected at 95-110° C. at 0.4 mmHg (16.63 g). A third fraction containing the acrylate product was collected as a colorless oil at 120-130° C. at 0.4 mmHg (13.51 g).

TABLE 1

Ratio of Isomers Present in Secondary Acrylate Product Examples (determined using Test Method 5).

| Example | 2-Isomer | 3-Isomer | 4-Isomer | 5+-Isomers |
|---|---|---|---|---|
| 1 | 79.1 | 20.0 | 0.9 | 0 |
| 9 | 76.8 | 19.1 | 3.1 | 1 |
| 10 | 74.8 | 20.1 | 3.8 | 1.3 |
| 11 | 75.5 | 19.6 | 3.9 | 1.0 |
| 12 | 43.9 | 24.3 | 13.2 | 18.6 |
| 13 | 22.5 | 24.4 | 19.1 | 34 |
| 14 | 53.1 | 31.3 | 15.6 | 0 |
| 15 | 49.1 | 29 | 12.2 | 9.7 |
| 16 | 43.0 | 23.5 | 17.7 | 15.8 |
| 17 | 66.7 | 23.7 | 6.3 | 3.3 |
| 18 | 52.5 | 24.8 | 11.1 | 11.6 |
| 19 | 77.9 | 18.3 | 2.9 | 0.9 |
| 20 | 59.0 | 24.7 | 9.2 | 7.1 |
| 21 | 75.6 | 18.3 | 2.9 | 3.2 |
| 22 | 62 | 26.3 | 7.6 | 4.1 |
| 23 | 23.0 | 23.0 | 17.8 | 36.2 |
| 24 | 19.9 | 21.1 | 15.0 | 44.0 |

Comparative Example 1

Batch Preparation of Octyl Acrylate Using 96% $H_2SO_4$

To 1.00 g (0.00891 mole, 1 eq) of 1-octene heated to 50° C. was added a solution of 0.706 g (0.00980 mole, 1.1 eq) of acrylic acid and 2.00 g of a 96 wt-% solution of sulfuric acid (18 M, 0.0196 mole, 2.2 eq). After 15 minutes at 70° C. all the olefin was consumed but only 30% of the product was the desired acrylate.

Comparative Example 2

Batch Preparation of Octyl Acrylate Using Methanesulfonic Acid

A mixture of 15.0 g (134 mmoles, 3 eq) of 1-octene, 3.21 g (44.6 mmoles, 1 eq) of acrylic acid, 0.257 g (2.67 mmoles, 0.06 eq) of methanesulfonic acid, 0.0277 g of MEHQ and 0.0034 g of copper(II) chloride dihydrate was heated at 105° C. for 22 hours to give 2.5% conversion to octyl acrylate based on acrylic acid consumed.

Comparative Example 3

Batch Preparation of Octyl Acrylate Using p-Toluenesulfonic Acid

A mixture of 15.0 g (134 mmoles, 3 eq) of 1-octene, 3.21 g (44.6 mmoles, 1 eq) of acrylic acid, 1.00 g (5.26 mmoles, 0.118 eq) of p-toluenesulfonic acid (monohydrate), 0.00277 g of MEHQ, and 0.0034 g of copper(II) chloride dihydrate was heated with stirring at 105° C. The mixture became homogeneous after 30 minutes. The mixture was heated at 105° C. for 20 hours. NMR indicated 38% conversion to octyl acrylate based on acrylic acid consumed. The reaction mixture produced a large amount of solids.

Comparative Example 4

Batch Preparation of 2-Dodecyl Acrylate from 2-Dodecanol

A mixture of 2-dodecanol (4.50 g, 24 mmol, Alfa-Aesar), triethylamine (2.81 g, 28 mmol), and methylene chloride (25 mL) was cooled in an ice bath. Acryloyl chloride (2.52 g, 28 mmol, Alfa-Aesar) was added dropwise over 30 minutes. The mixture was then stirred at room temperature for 17 hours, and then filtered. The mixture was diluted with ethyl acetate (100 mL) and washed successively with water and saturated sodium bicarbonate solution. The organic layer was concentrated to give the crude product, which was further purified by column chromatography over silica gel using 20 vol-% ethyl acetate in hexane. The final product was obtained as a slightly yellow oil (3.41 g).

Comparative Example 5

Batch Preparation of 2-Hexyldecyl Acrylate from 2-Hexadecanol

A mixture of 2-hexadecanol (4.50 g, 19 mmol, Alfa-Aesar), triethylamine (2.21 g, 22 mmol), and methylene chloride (60 mL) was cooled in an ice bath. Acryloyl chloride (2.02 g, 22 mmol, Alfa-Aesar) was added dropwise over 30 minutes. The mixture was then stirred at room temperature for 17 hours, and then filtered. The mixture was diluted with ethyl acetate (200 mL) and washed successively with aqueous sodium hydroxide (1.0 M) and brine solution. The organic layer was concentrated to give the crude product, which was further purified by column chromatography over silica gel using 10 vol-% ethyl acetate in hexane. The final product was obtained as a slightly yellow oil (3.04 g).

Other Comparative Monomers Used in Subsequent Examples

2-Ethylhexyl acrylate (2-EHA, Aldrich); isooctyl acrylate (IOA, 3M Company); n-butyl acrylate (nBA, Aldrich); lauryl acrylate (LA, Aldrich); octadecyl acrylate (ODA, Aldrich); and 2-octyl acrylate (2-OA, prepared according to preparatory Example 1 of U.S. Pat. No. 7,385,020).

Examples 25-37 and Comparative Examples 6-12

Thermal Properties of Acrylic Monomers

Acrylic monomers were analyzed using DSC following the procedure outlined in Test Method 1. The crystalline temperature (Tc) and melting temperature (Tm) were observed and recorded for each monomer. Samples that exhibited a Tc or Tm below the instrument capability of −100° C. are recorded as (<−100).

TABLE 2

Thermo Properties of Generated Acrylic Monomers

| Example | Monomer | Number of Carbons in Alkyl Chain | Isomer Type | Tc (° C.) | Tm (° C.) |
|---|---|---|---|---|---|
| CE6 | nBA | 4 | Primary | <−100 | <−100 |
| E25 | E1 | 8 | Secondary Blend | <−100 | <−100 |
| CE7 | 2-EHA | 8 | Primary | <−100 | <−100 |
| CE8 | IOA | 8 | Primary | <−100 | <−100 |
| E26 | E9 | 12 | Secondary Blend | −66 | −31 |
| E27 | E13 | 12 | Secondary Blend | <−100 | −59 |
| E28 | E17 | 12 | Secondary Blend | −70 | −72 |
| E29 | E18 | 12 | Secondary Blend | −79 | −48 |
| E30 | E23 | 12 | Secondary Blend | −90 | −54 |
| CE9 | CE4 | 12 | Secondary | −52.8 | −22 |
| CE10 | LA | 12 | Primary | −23.8 | 0.3 |
| E31 | E10 | 14 | Secondary Blend | −40.0 | −17 |
| E32 | E19 | 14 | Secondary Blend | −37 | −16 |
| E33 | E20 | 14 | Secondary Blend | −45 | −21 |
| E34 | E24 | 14 | Secondary Blend | −60 | −36 |
| E35 | E11 | 16 | Secondary Blend | −19 | −6 |
| E36 | E21 | 16 | Secondary Blend | −18 | −6 |
|  | E22 | 16 | Secondary Blend | −16 | −7 |
| CE11 | CE5 | 16 | Secondary | −7.0 | 6.7 |
| E37 | E12 | 18 | Secondary Blend | −7.6 | −1.8 |
| CE12 | ODA | 18 | Primary | 24.8 | 30.1 |

In Table 2, one can see that compared to single isomer monomers systems, the secondary acrylate blends generally have a lower crystalline temperatures. Furthermore, as the percentage of the 2-isomer decreases in the various secondary acrylate blends, the crystalline temperatures of these monomers decrease accordingly.

Examples 38-52 and Comparative Examples 13-19

Thermal Properties of Acrylic Homopolymers

Acrylic monomers generated in Examples 1 and 9-24 and Comparative Examples 4 and 5, and several other commercially available monomers, were converted to homopolymers and analyzed using DSC following the procedure outlined in Test Method 1. The crystalline temperature (Tc) and melting temperature (Tm) were observed and recorded for each monomer. Samples that exhibited a Tc or Tm below the instrument capability of −100° C. are recorded as (<−100).

TABLE 3

Thermo Properties of Generated Acrylic Homopolymers Using DSC

| Example | Monomer | Number of Carbons in Alkyl Chain | Isomer Type | Tc (° C.) | Tm (° C.) | Tg (° C.) |
|---|---|---|---|---|---|---|
| CE13 | nBA | 4 | Primary | <−100 | <−100 | −55 |
| CE14 | 2-EHA | 8 | Primary | <−100 | <−100 | −68 |
| CE15 | IOA | 8 | Primary | <−100 | <−100 | −65 |
| E38 | E1 | 8 | Secondary Blend | <−100 | <−100 | −51 |
| E39 | E14 | 8 | Secondary Blend | <−100 | <−100 | −50 |
| CE16 | LA | 12 | Primary | −7.9 | 3.9 | NO |
| CE17 | CE4 | 12 | Secondary | −48.8 | −46.1 | NO |
| E40 | E9 | 12 | Secondary | −76.0 | −76 | −60 |
| E41 | E13 | 12 | Secondary Blend | <−100 | <−100 | −61 |
| E42 | E17 | 12 | Secondary Blend | <−100 | <−100 | −57 |
| E43 | E18 | 12 | Secondary Blend | <−100 | <−100 | −57 |
| E44 | E23 | 12 | Secondary Blend | <−100 | <−100 | −62 |
| E45 | E10 | 14 | Secondary Blend | −40.0 | −27.5 | NO |
| E46 | E19 | 14 | Secondary Blend | −40 | −32 | NO |
| E47 | E20 | 14 | Secondary Blend | −48 | −39 | NO |
| E48 | E24 | 14 | Secondary Blend | −58 | −55 | −59 |
| CE18 | CE5 | 16 | Secondary | 1.7 | 5 | NO |
| E49 | E11 | 16 | Secondary Blend | −18.5 | −5.5 | NO |
| E50 | E21 | 16 | Secondary Blends | −19 | −3 | NO |
| E51 | E22 | 16 | Secondary Blends | −25 | −17 | NO |
| CE19 | ODA | 18 | Primary | 44 | 47 | NO |
| E52 | E12 | 18 | Secondary Blend | −5.0 | 3 | NO |

(NO) indicates not observed

Similar to the monomer crystalline temperature behavior in Table 2, it can be seen that the Tc in the formed polymers is significantly influenced by both monomer structure as well as the number of structural isomers in the monomer mixture. Again, as the percentage of the 2-isomer decreases in the various secondary acrylate blends, the Tc and Tm of the resulting polymer decreases accordingly.

Examples 53-54 and Comparative Examples 20-21

Adhesive Properties of Octyl Acrylate Based Pressure-Sensitive Adhesives

The acrylic monomers generated in Examples 1 and 10-12, 2-OA, 2-EHA, and LA were each prepared into adhesive films using the following procedure. The alkyl acrylate (28.5 g), 0.02 g of IRGACURE 651 (Ciba), 0.3 g of acrylic acid (AA, Alfa Aesar), and 1.2 g of hydroxyethyl acrylate (HEA, Aldrich) were mixed using a magnetic stir bar in a clear glass vial. The glass vial was then purged with nitrogen for 5 minutes to remove dissolved oxygen, and then treated with UV light (365 nm, approximately 5 mW/cm$^2$) until a coatable viscosity was achieved. The target for this step was an approximate viscosity of 3000 cP at room temperature and acrylic conversion of approximately 10%.

Each viscous sample was then formulated with additional IRGACURE 651, as well as a photocrosslinker, 2,4-bis(trichloromethyl)-6-(4-methoxyphenyl)-triazine (prepared according to Wakabayashi et al., *Bull. Chem. Soc. Jap.*, Vol. 42, pages 2924-2930 (1969), 12th example in Table 4). Additionally, tackifying resins were added such as a rosin ester based tackifier (FORAL 85E, Eastman Co.) or a hydrogenated aliphatic tackifier (REGALREZ 1094, Eastman Co.). In a typical procedure, 5 g of the viscous monomer formulation was added to an amber vial along with 2.5 g of REGALREZ 1094 tackifier (50 pph), 0.0045 g (0.09 pph) of IRGACURE 651 and 0.004 g (0.08 pph) of the photocrosslinker 2,4-bis(trichloromethyl)-6-(4-methoxyphenyl)-triazine. The amber vial was then rotated in the dark until the solid ingredients were completely dissolved. The resulting adhesive formulation was coated onto primed PET film at a coating thickness of 0.08 mm and covered with a silicone treated release liner. This construction was then placed under a bank of UV lights and cured using approximately 600 mJ/cm$^2$ of UV irradiation. This procedure was repeated for each additional adhesive formulation. Adhesive coated sheets were tested for clarity, peel, and shear strength according to Test Methods 2, 3, and 4 above.

TABLE 4

Adhesive Properties of PSAs Generated From Octyl Acrylate

| Example | Monomer | Tackifier FORAL 85E (pph) | Visual Appearance After Cure | 180° Peel on Stainless Steel (N/dm.) | 70° C. Shear on Stainless Steel (min) |
|---|---|---|---|---|---|
| E53 | E1 | 0 | Clear | 48 | +10,000 |
| E54 | E1 | 15 | Clear | 97 | N.T. |
| CE20 | 2-OA | 0 | Clear | 49 | +10,000 |
| CE21 | 2-OA | 15 | Clear | 94 | N.T. |

As shown in Table 4, there is no significant difference in adhesive properties of formulation based on Example 1 or 2-OA. However, as stated above, 1-octene is significantly less expensive than 2-octanol, potentially leading to a less expensive route to the acrylic monomer and ultimately to a PSA with equivalent performance but lower cost.

Examples 55-60 and Comparative Examples 22-27

Adhesive Properties of Acrylates

TABLE 5

Adhesive Properties of PSAs Generated From Long Chain Acrylate Examples

| Example | Monomer | Number of Carbons in Alkyl Chain | Tackifier REGALREZ ™ 1094 (pph) | Visual Appearance After Cure | 180° Peel on S. Steel (N/dm.) | 180° Peel on HDPE (N/dm.) |
|---|---|---|---|---|---|---|
| E55 | E10 | 14 | 50 | Clear | 48 | 46 |
| E56 | E10 | 14 | 75 | Clear | 53 | 51 |
| E57 | E10 | 14 | 85 | Clear | 45 | 39 |
| E58 | E11 | 16 | 50 | Clear | 51 | 41 |
| E59 | E11 | 16 | 75 | Clear | 74 | 58 |

TABLE 5-continued

Adhesive Properties of PSAs Generated From Long Chain Acrylate Examples

| Example | Monomer | Number of Carbons in Alkyl Chain | Tackifier REGALREZ™ 1094 (pph) | Visual Appearance After Cure | 180° Peel on S. Steel (N/dm.) | 180° Peel on HDPE (N/dm.) |
|---|---|---|---|---|---|---|
| E60 | E11 | 16 | 85 | Clear | 73 | 59 |
| CE22 | 2-EHA | 8 | 50 | opaque | 22 | 23 |
| CE23 | 2-EHA | 8 | 75 | opaque | 4 | 4 |
| CE24 | 2-EHA | 8 | 85 | opaque | 14 | 1 |
| CE25 | LA | 12 | 50 | opaque | 27 | 24 |
| CE26 | LA | 12 | 75 | opaque | 38 | 34 |
| CE27 | LA | 12 | 85 | opaque | 44 | 44 |

Table 5 shows that PSA films generated using the monomers of this disclosure are compatible (visually clear coatings) with high loadings of non-polar REGALREZ 1094 tackifier. In addition, these examples exhibit excellent peel strength on both stainless steel and high density polyethylene (HDPE), which is a very low surface energy substrate to which (meth)acrylic ester PSAs typically have difficulty adhering.

The complete disclosures of the patents, patent documents, and publications cited herein are incorporated by reference in their entirety as if each were individually incorporated. Various modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only with the scope of the disclosure intended to be limited only by the claims set forth herein as follows.

The invention claimed is:

1. A pressure-sensitive adhesive composition comprising a (meth)acrylate polymer comprising interpolymerized monomers comprising at least three structural isomers of a secondary alkyl (meth)acrylate of Formula (I):

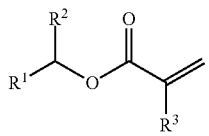

wherein:
  $R^1$ and $R^2$ are each independently a $C_1$ to $C_{30}$ saturated linear alkyl group;
  the sum of the number of carbons in $R^1$ and $R^2$ is 7 to 31; and
  $R^3$ is H or $CH_3$.

2. The pressure-sensitive adhesive of claim 1 wherein the at least three structural isomers of an alkyl (meth)acrylate of Formula (I) comprise:
  15-85 mole-% of a 2-alkyl (meth)acrylate isomer;
  5-50 mole-% of a 3-alkyl (meth)acrylate isomer;
  0.5-40 mole-% of a 4-alkyl (meth)acrylate isomer; and
  0-50 mole-% of at least one of a 5- through 15-alkyl (meth)acrylate isomer;
wherein the mole percentages are based on the total moles of (meth)acrylate isomers used to make the polymer.

3. The pressure-sensitive adhesive of claim 1 which has a Tc of ≤0° C.

4. A pressure-sensitive adhesive article comprising a coating of the pressure-sensitive adhesive of claim 1 on a backing.

5. A (meth)acrylate polymer comprising interpolymerized monomers comprising:
  a) at least three structural isomers of a secondary alkyl (meth)acrylate of Formula (I):

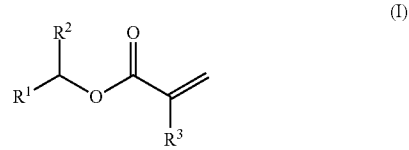

wherein:
  $R^1$ and $R^2$ are each independently a $C_1$ to $C_{30}$ saturated linear alkyl group;
  the sum of the number of carbons in $R^1$ and $R^2$ is 7 to 31; and
  $R^3$ is H or $CH_3$; and
  b) at least one monomer selected from:
    i) a (meth)acrylic acid ester of a $C_1$-$C_{32}$ alkanol;
    ii) an acid-functional, ethylenically unsaturated monomer;
    iii) a non-acid-functional, ethylenically unsaturated polar monomer;
    iv) a vinyl monomer; and
    v) a multifunctional (meth)acrylate.

6. The (meth)acrylate polymer of claim 5 wherein the interpolymerized monomers comprise at least one monomer selected from a (meth)acrylic acid ester of a $C_1$-$C_{32}$ alkanol, an acid-functional, ethylenically unsaturated monomer, a non-acid-functional, ethylenically unsaturated polar monomer, and a mixture thereof.

7. The (meth)acrylate polymer of claim 6 wherein the interpolymerized monomers comprise an acid-functional, ethylenically unsaturated monomer.

8. The (meth)acrylate polymer of claim 7 wherein the interpolymerized monomers comprise:
  a) 20 to 99.5 parts by weight of the at least three structural isomers of a secondary alkyl (meth)acrylate of Formula (I); and
  b) 0 to 80 parts by weight of a (meth)acrylic acid ester of a $C_1$-$C_{32}$ alkanol;
  c) 0.5 to 20 parts by weight of an acid-functional, ethylenically unsaturated monomer;
  d) 0 to 10 parts by weight of a non-acid-functional, ethylenically unsaturated polar monomer;

e) 0 to 5 parts by weight of a vinyl monomer; and
f) 0 to 5 parts by weight of a multifunctional (meth)acrylate;
based on 100 parts by weight total monomer.

9. A mixture of structural isomers of a secondary alkyl (meth)acrylate of Formula (I):

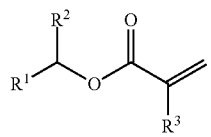
(I)

wherein:
$R^1$ and $R^2$ are each independently a $C_1$ to $C_{30}$ saturated linear alkyl group;
the sum of the number of carbons in $R^1$ and $R^2$ is 7 to 31; and
$R^3$ is H or $CH_3$;
wherein the 2-alkyl (meth)acrylate isomer is less than 35 mole-% of the total mixture of alkyl (meth)acrylate isomers.

10. A method of making a mixture of structural isomers of a secondary alkyl (meth)acrylate of Formula (I):

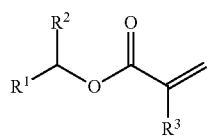
(I)

wherein:
$R^1$ and $R^2$ are each independently a $C_1$ to $C_{30}$ saturated linear alkyl group;
the sum of the number of carbons in $R^1$ and $R^2$ is 7 to 31; and
$R^3$ is H or $CH_3$;
wherein the method comprises reacting (meth)acrylic acid with an olefin having a single unsaturation in the presence of a fluorinated sulfonic acid.

11. A method of making a mixture of structural isomers of a secondary alkyl (meth)acrylate of Formula (I):

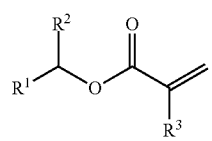
(I)

wherein:
$R^1$ and $R^2$ are each independently a $C_1$ to $C_{30}$ saturated linear alkyl group;
the sum of the number of carbons in $R^1$ and $R^2$ is 7 to 31; and
$R^3$ is H or $CH_3$;
wherein the method involves reacting (meth)acrylic acid with an olefin having a single unsaturation, wherein the olefin has been pre-treated with an acid to give a mixture of olefin isomers.

12. The method of claim 11, wherein reacting (meth)acrylic acid with the olefin having the single unsaturation occurs in a continuous process.

13. The method of claim 12, wherein the continuous process uses a packed-bed reactor with a solid acid catalyst.

* * * * *

UNITED STATES PATENT AND TRADEMARK OFFICE
CERTIFICATE OF CORRECTION

PATENT NO.         : 9,102,774 B2                                           Page 1 of 1
APPLICATION NO.    : 13/881526
DATED              : August 11, 2015
INVENTOR(S)        : Clapper et al.

It is certified that error appears in the above-identified patent and that said Letters Patent is hereby corrected as shown below:

In the specification

Column 8
Line 48, delete "9-heneicosene," and insert -- 9-heneicosane, --, therefor.

Column 11
Line 57, delete "parrafins" and insert -- paraffins --, therefor.

Column 15
Line 45, delete "N-vinylpyrrolidinone," and insert -- N-vinylpyrrolidone, --, therefor.

Column 24
Line 23, delete "9-heneicosene," and insert -- 9-heneicosane, --, therefor.

Column 27
Line 65, delete "1-10 ton)" and insert -- 1-10 torr) --, therefor.

Column 28
Line 15, delete "Octel" and insert -- Octyl --, therefor.

Signed and Sealed this
Twelfth Day of April, 2016

Michelle K. Lee
*Director of the United States Patent and Trademark Office*